United States Patent
Stout et al.

(10) Patent No.: US 11,364,513 B2
(45) Date of Patent: Jun. 21, 2022

(54) AROMATIC FOG GENERATOR FOR BATHING ENVIRONMENTS

(71) Applicant: Kohler Co., Kohler, WI (US)

(72) Inventors: Kenneth L. Stout, Sheboygan Falls, WI (US); Stephen J. Bowen, Sheboygan, WI (US)

(73) Assignee: KOHLER CO., Kohler, WI (US)

( * ) Notice: Subject to any disclaimer, the term of this patent is extended or adjusted under 35 U.S.C. 154(b) by 259 days.

(21) Appl. No.: 16/675,994

(22) Filed: Nov. 6, 2019

(65) Prior Publication Data

US 2020/0139388 A1    May 7, 2020

Related U.S. Application Data

(60) Provisional application No. 62/757,001, filed on Nov. 7, 2018.

(51) Int. Cl.

| B05B 7/04 | (2006.01) |
|---|---|
| A47K 3/02 | (2006.01) |
| A47K 3/00 | (2006.01) |
| B05B 17/06 | (2006.01) |
| A61L 9/12 | (2006.01) |
| B05B 7/00 | (2006.01) |
| A61L 9/14 | (2006.01) |
| A61H 33/00 | (2006.01) |

(52) U.S. Cl.
CPC ............... *B05B 7/04* (2013.01); *A47K 3/001* (2013.01); *A47K 3/02* (2013.01); *A61H 33/00* (2013.01); *A61L 9/122* (2013.01); *A61L 9/125* (2013.01); *A61L 9/14* (2013.01); *B05B 7/0081* (2013.01); *B05B 17/0607* (2013.01); *A61H 2201/0188* (2013.01); *A61H 2201/102* (2013.01); *A61L 2209/11* (2013.01)

(58) Field of Classification Search
CPC ..... B05B 7/04; B05B 7/0081; B05B 17/0607; A47K 3/001; A47K 3/02; A61H 33/00; A61H 2201/0188; A61H 2201/102; A61L 9/122; A61L 9/125; A61L 9/14; A61L 2209/11

See application file for complete search history.

(56) References Cited

U.S. PATENT DOCUMENTS

| 4,603,030 | A  | 7/1986  | McCarthy   |
|---|---|---|---|
| 5,023,020 | A  | 6/1991  | Machida    |
| 5,565,148 | A  | 10/1996 | Pendergrass |
| 6,581,915 | B2 | 6/2003  | Bartsch    |
| 6,619,559 | B2 | 9/2003  | Wohrle     |
| 6,712,287 | B1 | 3/2004  | Le Pesant  |
| 6,783,117 | B2 | 8/2004  | Wohrle     |
| 6,834,847 | B2 | 12/2004 | Bartsch    |
| 7,610,118 | B2 | 10/2009 | Schramm    |
| 7,622,073 | B2 | 11/2009 | Schramm    |
| 7,734,159 | B2 | 6/2010  | Beland     |
| 8,016,207 | B2 | 9/2011  | Kvietok    |
| 8,170,405 | B2 | 5/2012  | Harris     |

(Continued)

*Primary Examiner* — Tuan N Nguyen
(74) *Attorney, Agent, or Firm* — Foley & Lardner LLP

(57) ABSTRACT

A fog generator assembly includes a water vapor generator, a fragrance dispenser, and a mixing element fluidly coupled to the water generator and the fragrance dispenser. The mixing element is configured to mix a fog of water vapor from the water vapor generator with a fragrance from the fragrance dispenser to produce an aromatic fog.

20 Claims, 34 Drawing Sheets

(56) References Cited

U.S. PATENT DOCUMENTS

| | | |
|---|---|---|
| 8,266,738 B2 | 9/2012 | Castellote |
| 9,453,652 B2 | 9/2016 | Neumann |
| 9,523,185 B2 | 12/2016 | Brunelle |
| 9,814,358 B2 | 11/2017 | Brunelle |
| 2003/0107139 A1 | 6/2003 | Wohrle |
| 2004/0007787 A1 | 1/2004 | Kvietok |
| 2005/0217016 A1 | 10/2005 | Ciechanowski |
| 2008/0223953 A1* | 9/2008 | Tomono ............... A61L 9/145 239/102.2 |
| 2011/0110824 A1 | 5/2011 | Hsiao |
| 2017/0246336 A1* | 8/2017 | Suissa ............... A61L 9/14 |
| 2018/0169288 A1 | 6/2018 | Kelsen |

\* cited by examiner

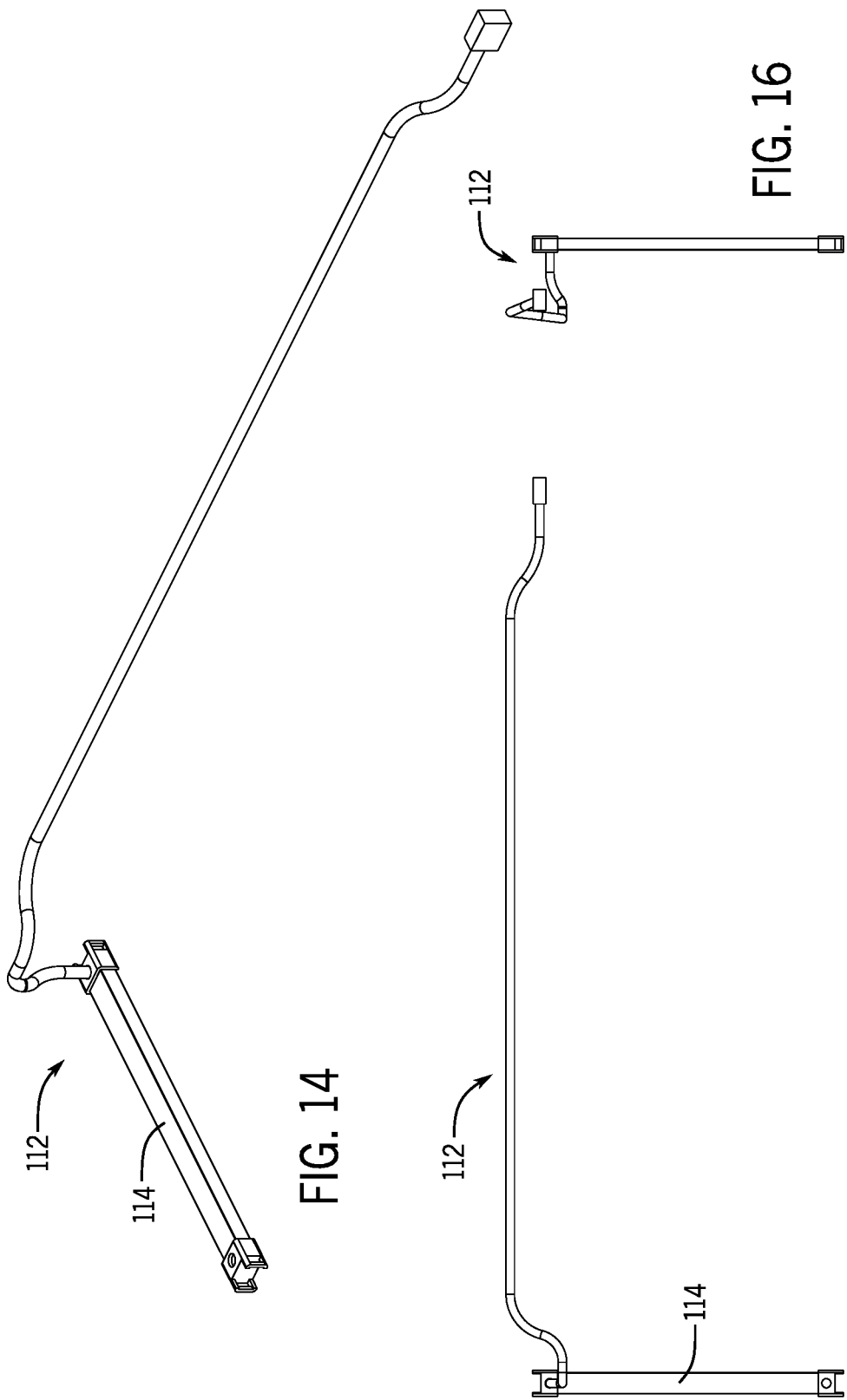

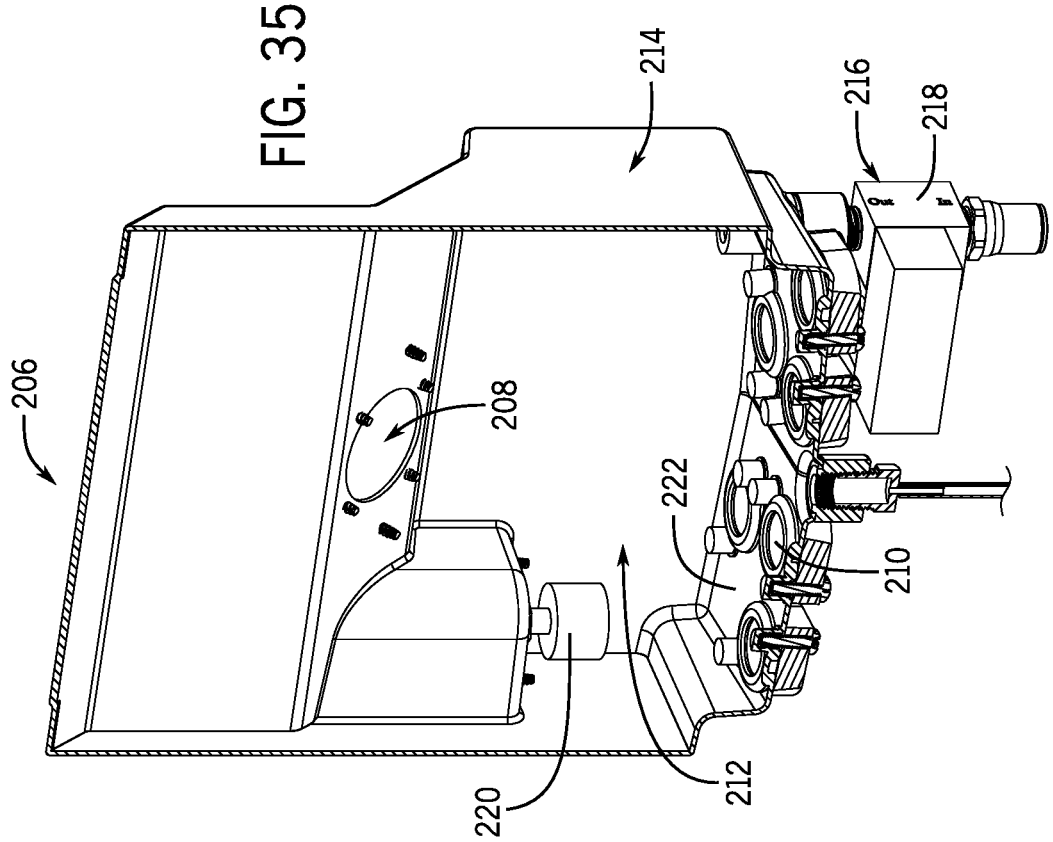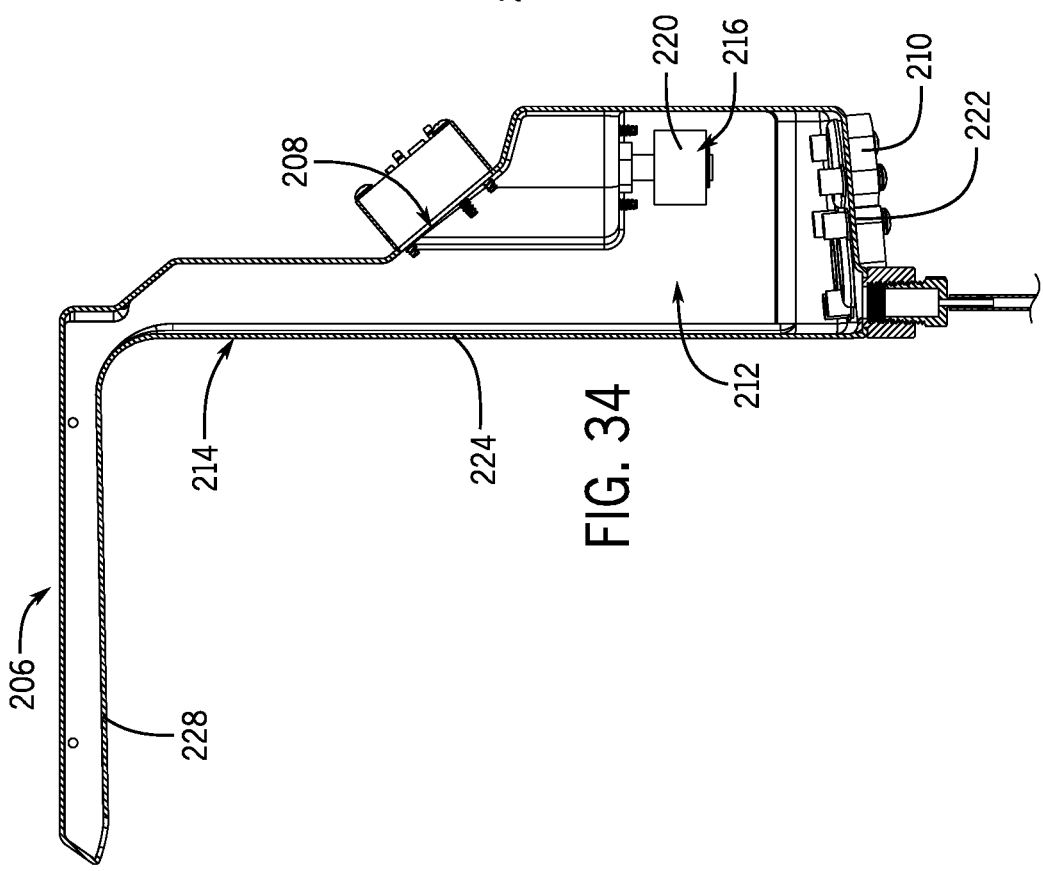

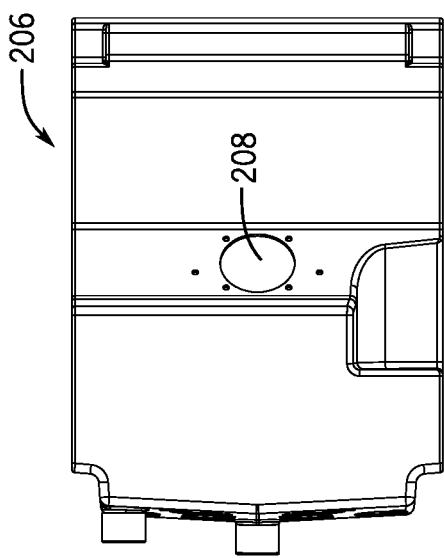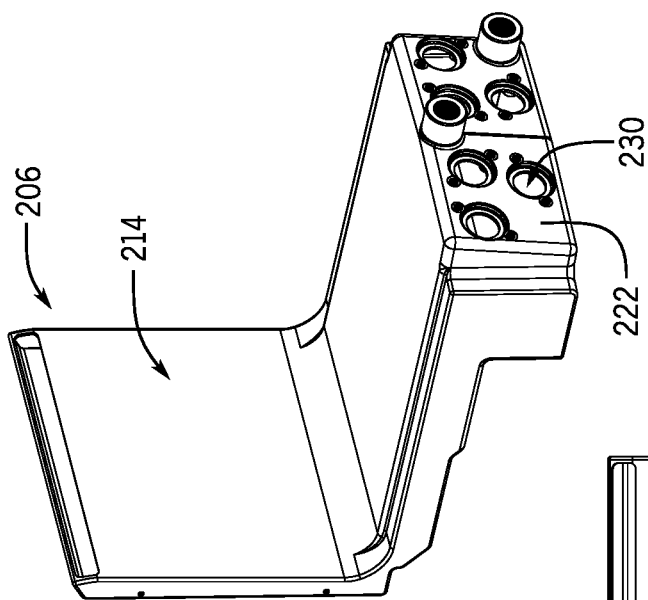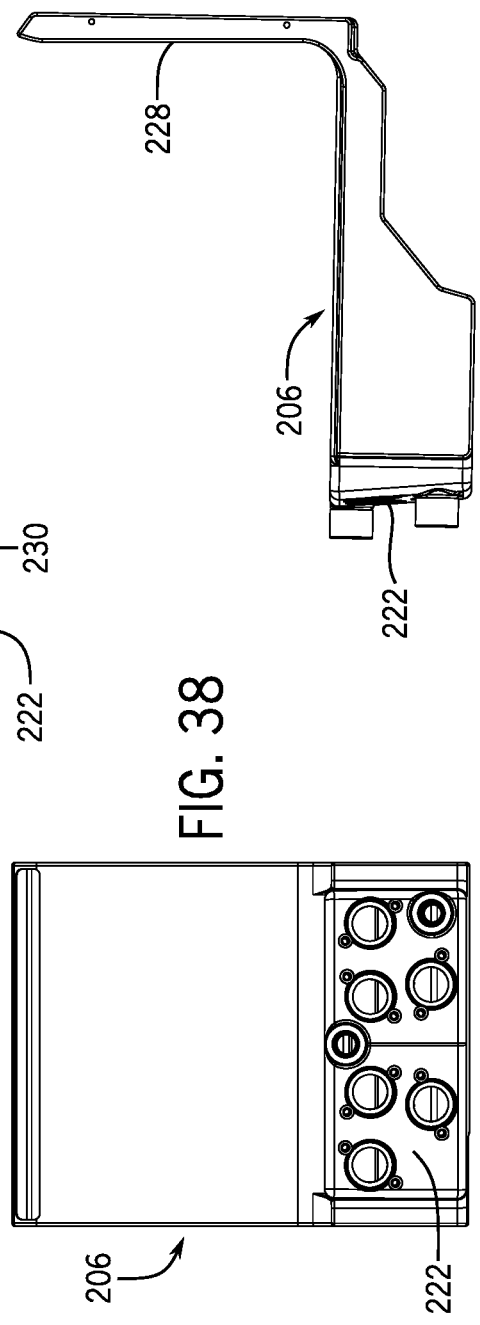

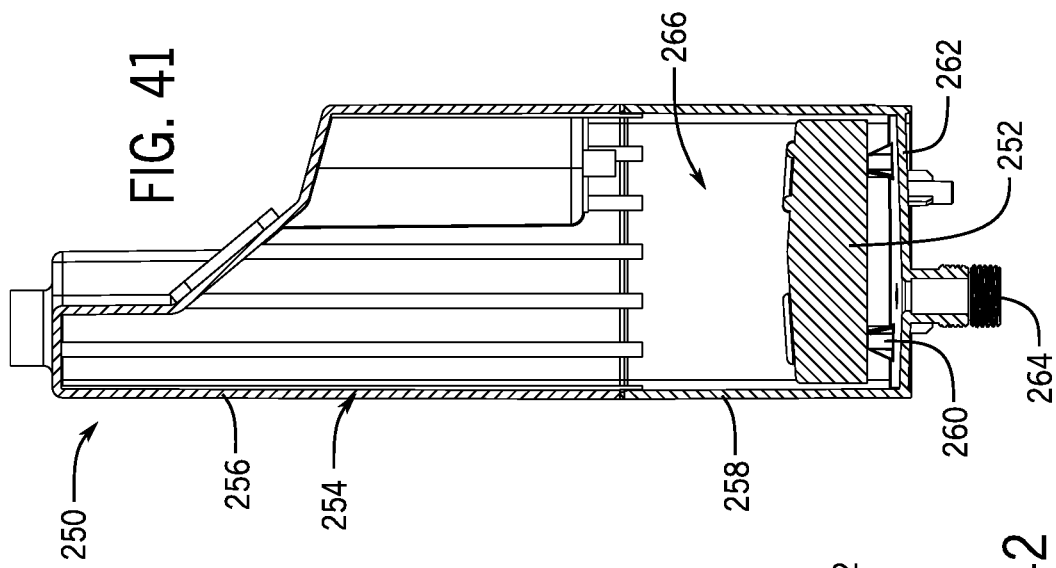
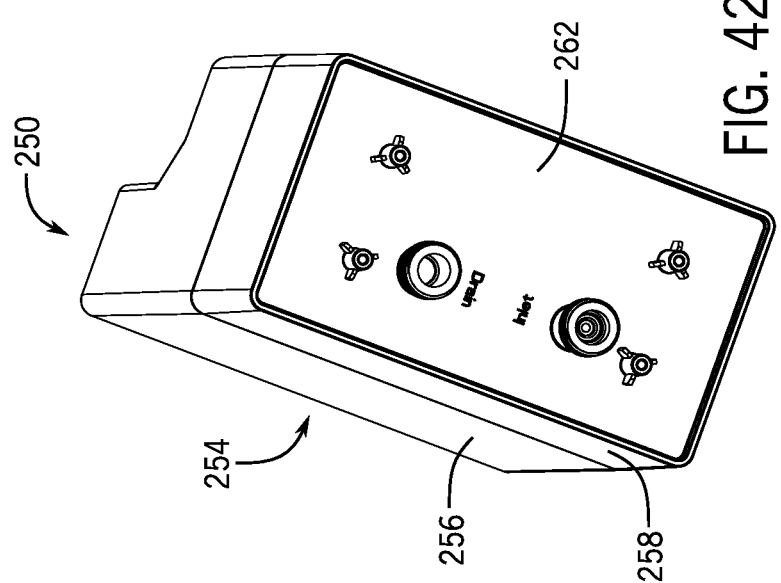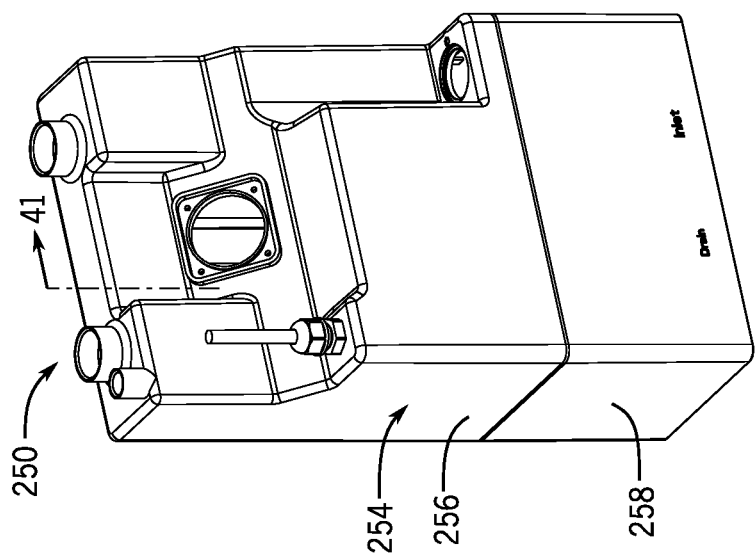

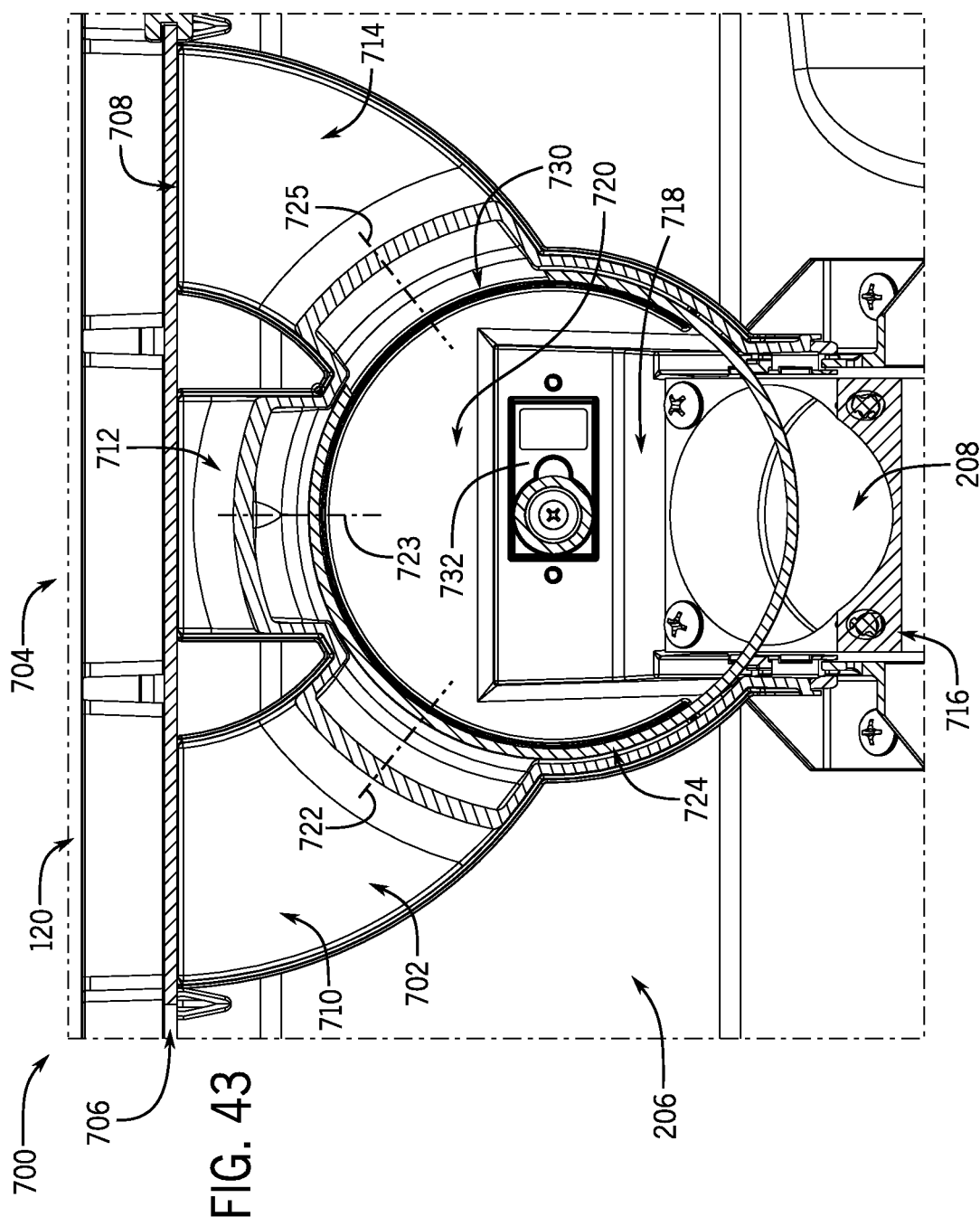

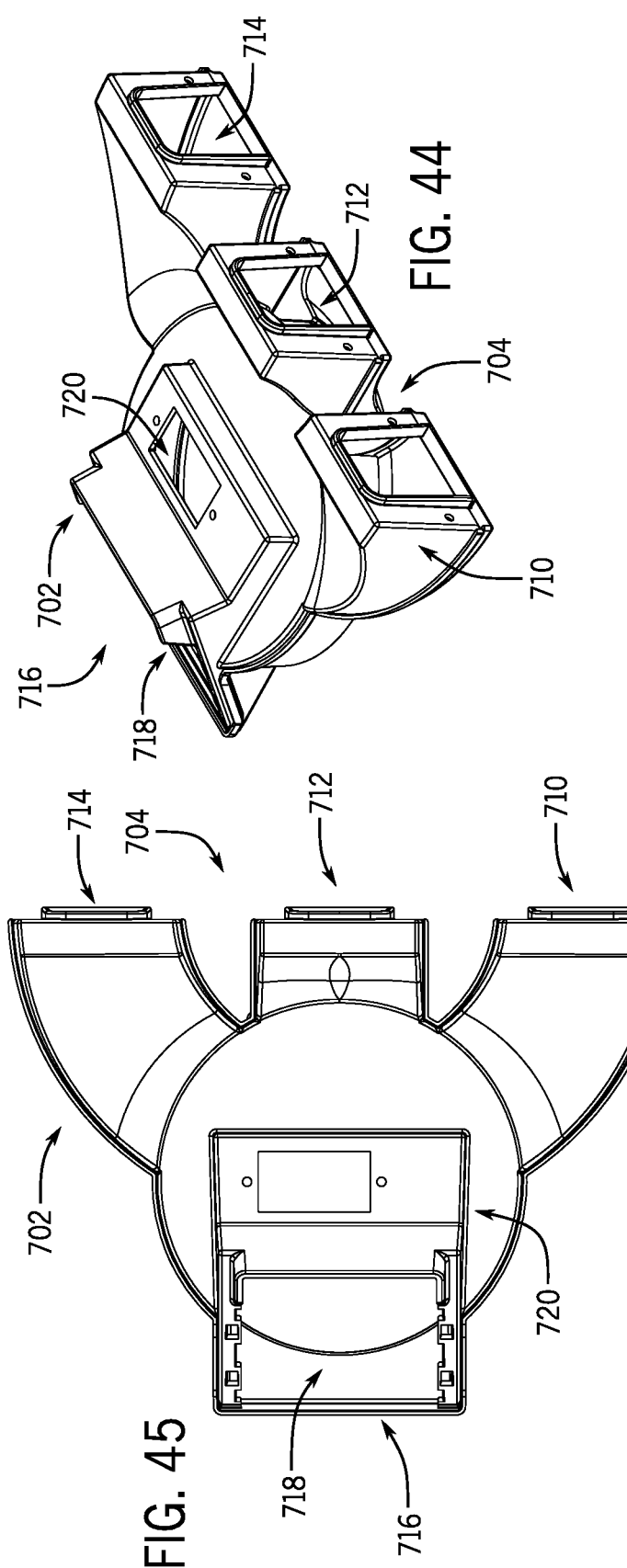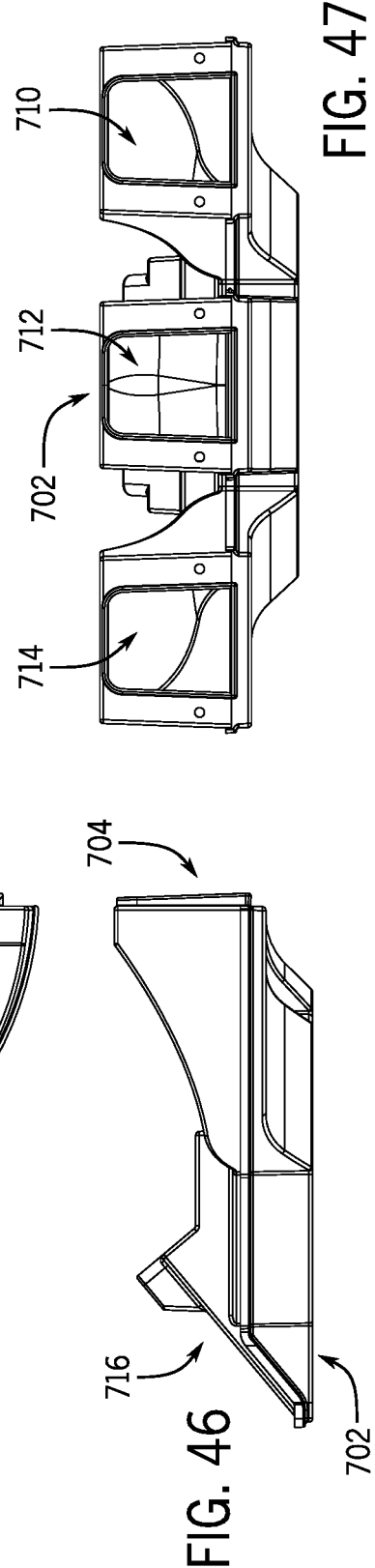

AROMATIC FOG GENERATOR FOR BATHING ENVIRONMENTS

CROSS-REFERENCE TO RELATED PATENT APPLICATIONS

The application claims the benefit of and priority to U.S. Provisional Patent Application No. 62/757,001, filed Nov. 7, 2018, the entire disclosure of which is hereby incorporated by reference herein.

BACKGROUND

The present disclosure relates generally to systems used in a bath or shower environment to improve a user's bathing experience. More specifically, the present disclosure relates to a fog generator assembly that has the capability to dispense different aromas/scents in a bath or shower environment.

Conventional aromatic dispensing devices utilize a single aromatic, which may be provided in the form of an essential oil or a mixture of essential oils. The oil or oil mixture is traditionally stored in a small cavity within the device. The device may include heating elements contained within a base of the cavity to facilitate the release of the scent by vaporizing the essential oils. The dispensing device is typically activated manually; for example, by using a simple on/off toggle located on the device.

SUMMARY

One exemplary embodiment relates to a fog generator assembly. The fog generator assembly includes a water vapor generator, a fragrance dispenser, and a mixing element. The mixing element is fluidly coupled to the water vapor generator and the fragrance dispenser. The mixing element is configured to mix a fog of water vapor from the water vapor generator with a fragrance from the fragrance dispenser to produce an aromatic fog. The mixing element may be configured to deliver the aromatic fog to a space above a bath.

In some embodiments, the fragrance dispenser is fluidly coupled to an environment surrounding the fog generator assembly. The fog generator assembly may further include an air displacement device that moves air through the fragrance dispenser. In some implementations an amount of aromatic fog provided by the mixing element is controlled by the air displacement device.

Another exemplary embodiment relates to a bathing system. The bathing system includes a bath and a fog generator assembly disposed adjacent to the bath. The fog generator assembly includes a water vapor generator, a fragrance dispenser, and a mixing element. The mixing element is fluidly coupled to the water vapor generator and the fragrance dispenser. The mixing element is configured to mix a fog of water vapor from the water vapor generator with a fragrance from the fragrance dispenser to produce an aromatic fog.

BRIEF DESCRIPTION OF THE FIGURES

FIG. 14 is a perspective view of a light source for the fog generator assembly of FIG. 3, according to an exemplary embodiment.

FIG. 15 is a back view of the light source of FIG. 14.

FIG. 16 is a top view of the light source of FIG. 14.

FIG. 34 is a side cross-sectional view of the fog generator subassembly of FIG. 32.

FIG. 35 is a perspective cross-sectional view of the fog generator subassembly of FIG. 32.

FIG. 36 is a perspective view of a housing assembly for the fog generator subassembly of FIG. 32, according to an exemplary embodiment.

FIG. 37 is a back view of the housing assembly of FIG. 36.

FIG. 38 is a bottom view of the housing assembly of FIG. 36.

FIG. 39 is a side view of the housing assembly of FIG. 36.

FIG. 40 is a top perspective view of a housing assembly for a fog generator subassembly, according to another exemplary embodiment.

FIG. 41 is a side cross-sectional view of the housing assembly of FIG. 40.

FIG. 42 is a bottom perspective view of the housing assembly of FIG. 40.

FIG. 43 is a back cross-sectional view of a valve for the fog generator subassembly of FIG. 32, according to an exemplary embodiment.

FIG. 44 is a perspective view of a manifold for the fog generator subassembly of FIG. 32, according to an exemplary embodiment.

FIG. 45 is a front view of the manifold of FIG. 44.

FIG. 46 is a side view of the manifold of FIG. 44.

FIG. 47 is a top view of the manifold of FIG. 44.

DETAILED DESCRIPTION

Figure 1:
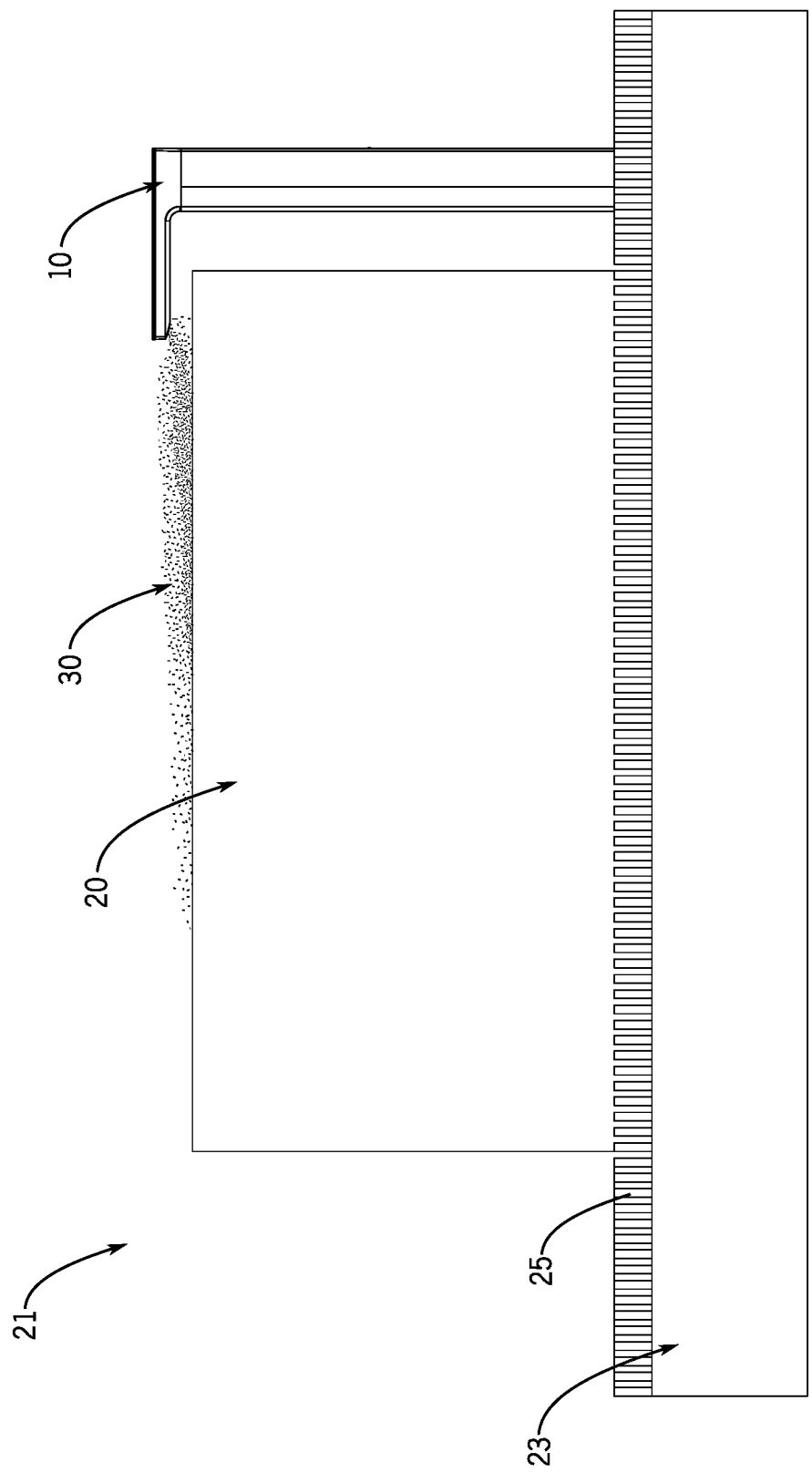
FIG. 1 is a side view of a whirlpool bath and fog generator assembly, according to an exemplary embodiment.

Referring generally to the figures, a fog generator assembly is configured to mix the fog of water vapor with a fragrance or mixture of fragrances and distribute the aromatic fog to a user occupied space above a bath. The fog generator assembly may be configured to select and deliver one fragrance or a mixture of different fragrances in sequence. According to an exemplary embodiment, the fog generator assembly includes an aromatic sequence control system configured to facilitate the operation of the fog generator assembly.

In some embodiments, the fog generator assembly includes a fog tank configured to contain a predetermined volume of water. A lower wall of the fog tank may be sloped. In some exemplary embodiments, the fog generator assembly includes a water delivery and metering system. The water delivery and metering system may include a continuous drain.

The fog generator assembly is configured to provide an aromatic mist of water vapor in a bath or shower environment. In some embodiments, the fog generator assembly is a self-contained unit separate from the bath. According to an exemplary embodiment, the assembly is configured as an assembly that extends substantially upright from a supporting surface for the bath. An upper portion of the assembly extends substantially horizontally above the bath so as to distribute an aromatic fog to a user occupied space above a waterline in the bath. Among other benefits, the aromatic fog provides a cooling effect to the user who may otherwise become overheated in the bath.

According to an exemplary embodiment, the fog generator assembly includes a water vapor generating portion (e.g., a water vapor generator), an aromatic dispensing portion (e.g., a fragrance dispenser) fluidly coupled to the water vapor generating portion, and a mixing portion (e.g., a mixing element) fluidly coupled to both the water vapor generating portion and the aromatic dispensing portion. The water vapor generating portion includes a water delivery and metering system. The delivery and metering system is configured to provide and control the level of water in an inner cavity. The metering system may include a continuous drain as well as an overflow drain. In some exemplary embodiments, the fog generator assembly may include a base and a cover disposed thereon. The cover may be configured to guide the flow of water into and out of an inner cavity of the base. The water vapor generating portion also includes a plurality of ultrasonic devices configured to vaporize water contained within an inner cavity.

The aromatic dispensing portion is configured to deliver a plurality of fragrances to enhance the user's bathing experience. The aromatic dispensing portion may be automatically controlled from a mobile computing device (e.g., an internet of things (IoT) device, a mobile phone, a laptop computer, etc.). In other exemplary embodiments, the aromatic dispensing portion may be automatically controlled from a user interface disposed on the fog generator assembly. In yet other exemplary embodiments, the aromatic dispensing portion may be controlled from a handheld remote for the fog generator assembly. The aromatic dispensing portion may be configured to provide multiple fragrances in a user-customized or pre-programmed sequence. The fragrances may be generated by convective mass transfer of one, or a plurality of, essential oils into a flowing stream of air.

The amount/quantity of aroma and/or fog that is produced may be varied by controlling the flow rate of air (e.g., a fan speed, etc.) and/or by controlling one or more of the plurality of ultrasonic devices (e.g., by activating/deactivating one or more ultrasonic devices and/or varying the voltage or operating frequency of one or more ultrasonic devices). Among other benefits, the aromatic dispensing portion does not rely on heaters or other powered equipment to facilitate the release of fragrances from the essential oils, as compared to conventional aromatic dispensing devices. The fragrance is introduced into the mixing portion to generate the aromatic fog, which is then distributed into the user occupied space. Providing the various fragrances in sequence contributes to an enhanced sensory effect as compared to a single scent, which the user may otherwise become accustomed to after a short period of exposure. Advantageously, the aromatic dispensing portion is capable of mixing together different scents from single containers of essential oils to form an aromatic mixture, thereby significantly increasing the variety of fragrances that may be delivered.

Another exemplary embodiment relates to a method of operation for a fog generator assembly. The method includes receiving a control signal from a remote device, activating one or more ultrasonic devices, fans, lights, and a manifold valve member based on the control signal. The method includes querying the control signal. The method includes monitoring the control signal for a shut-down command and a change command. The change command may result in the modification of one or more operating parameters for the fog generator subassembly.

In some exemplary embodiments, the fog generator assembly is part of a whirlpool bathing system that includes a whirlpool bath. The whirlpool bathing system may further include a whirlpool filtration system configured to filter (e.g., remove) visible particulate from the whirlpool bath and improve water cleanliness. The filtration system may be a retrofit filtration system for use in an existing whirlpool bath that was not originally designed to receive a filter. More specifically, the filtration system may be incorporated into an existing suction fitting of the whirlpool bath used as part of the water recirculation system for the whirlpool bath. The filtration system may be concealed from a user's view by the suction fitting and/or other parts of the bath or recirculation system. The filtration system includes a removable filter that allows a user to easily replace the filter once it becomes clogged. These and other advantageous features will become apparent to those reviewing the present disclosure and figures.

Referring to FIGS. 1-4, a fog generator assembly is illustrated as assembly 10 according to an exemplary embodiment. As shown in FIG. 1, the assembly 10 is disposed alongside a bath 20 (e.g., a whirlpool, tub, etc.) and is a separate fixture from the bath 20. The bath 20 may form part of a whirlpool bathing system 21. The assembly 10 includes a substantially vertical support structure, shown as housing 100, coupled to a support surface for the bath 20. In an exemplary embodiment, the support surface is a bathroom and/or shower floor. In other exemplary embodiments, as shown in FIG. 1, the support surface is a pedestal 23 (e.g., platform, etc.) for the bath 20. In some embodiments, the bath 20 and the pedestal 23 cooperatively form an overflowing bath in which water flows over an upper edge of the bath 20, along a perimeter of the bath 20, and falls, via gravity, onto the pedestal 23. The pedestal 23 is disposed between the bath and the floor and completely surrounds the bath 20 so that any water flowing over the edge of the bath 20 is received on an upper surface of the pedestal 23. The pedestal 23 includes a plurality of slats 25 (e.g., rectangular extensions, etc.) that are distributed across the upper surface. The slats 25 are spaced apart from one another forming openings so that water may flow in between the slats 25 and into the pedestal 23 (e.g., an interior portion of the pedestal 23). The slats 25 provide a surface for the user to step on when entering the bath 20 and improve the overall aesthetic of the bath 20. In other embodiments, the design of the water receiving portion of the pedestal 23 may be different (e.g., the shape of the slats 25, the number of slats 25, the spacing of the slats 25 across the upper surface of the pedestal 23, etc.). The pedestal 23 redirects the flow of water received through the openings between slats to a drain or to a suction fitting for recirculation back into the bath 20. In some embodiments, the fog generator assembly 10 forms part of a faucet for the bath 20 and provides water to the bath 20 in addition to the fog and/or aroma.

Figure 2:
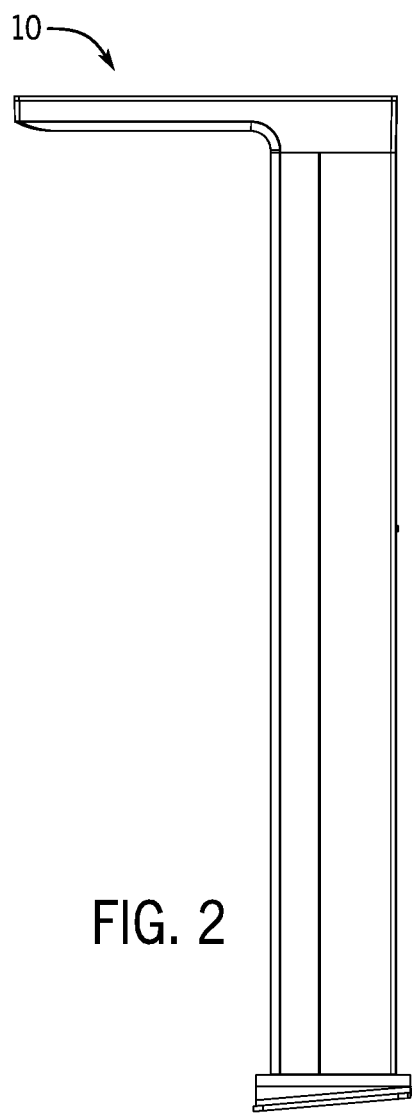
FIG. 2 is a side view of a fog generator assembly configured to mount to a raised surface, according to an exemplary embodiment.
Figure 3:
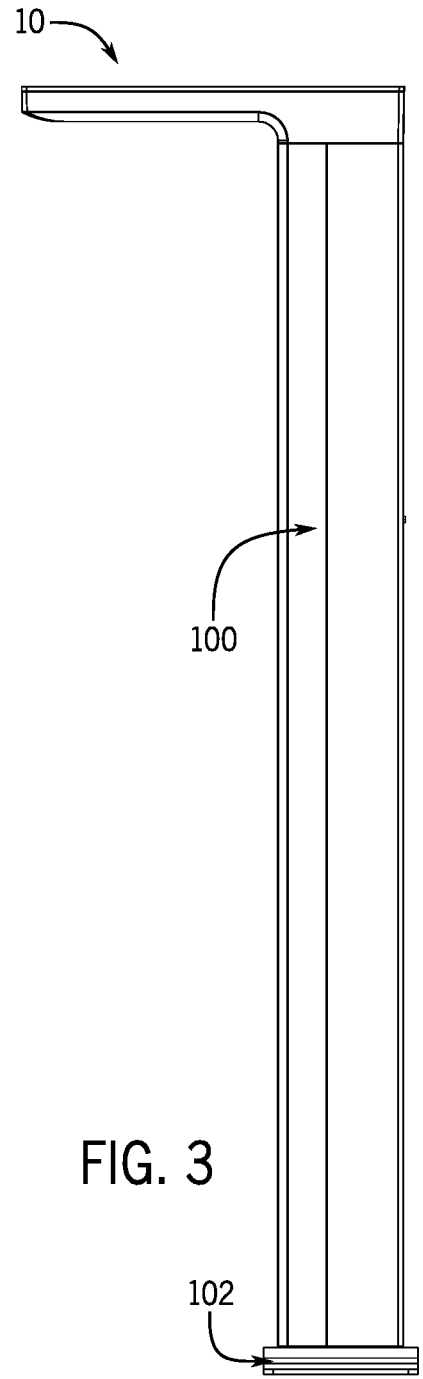
FIG. 3 is a side view of a fog generator assembly configured to mount to a floor surface, according to an exemplary embodiment.

As shown in FIGS. 2-3, a height of the assembly 10 may be modified to suit the requirements of a given space; for example, the height of the assembly 10 may be greater than a height of the bath 20, so as to dispense a fog of water vapor into a user occupied space above the bath 20 (e.g., a space above a waterline of the bath proximate to where the user's head may be located). In this position (in the user occupied space above the bath 20), the exposed body-parts of the user will be in direct contact with the fog of water vapor, which can, advantageously, provide a cooling effect to the user. Furthermore, dispensing the fog into the user occupied space above the bath 20 may, advantageously, place the fog in proximity to the user's nose and mouth, and thereby more fully expose the user to the pleasant fragrance.

Figure 4:
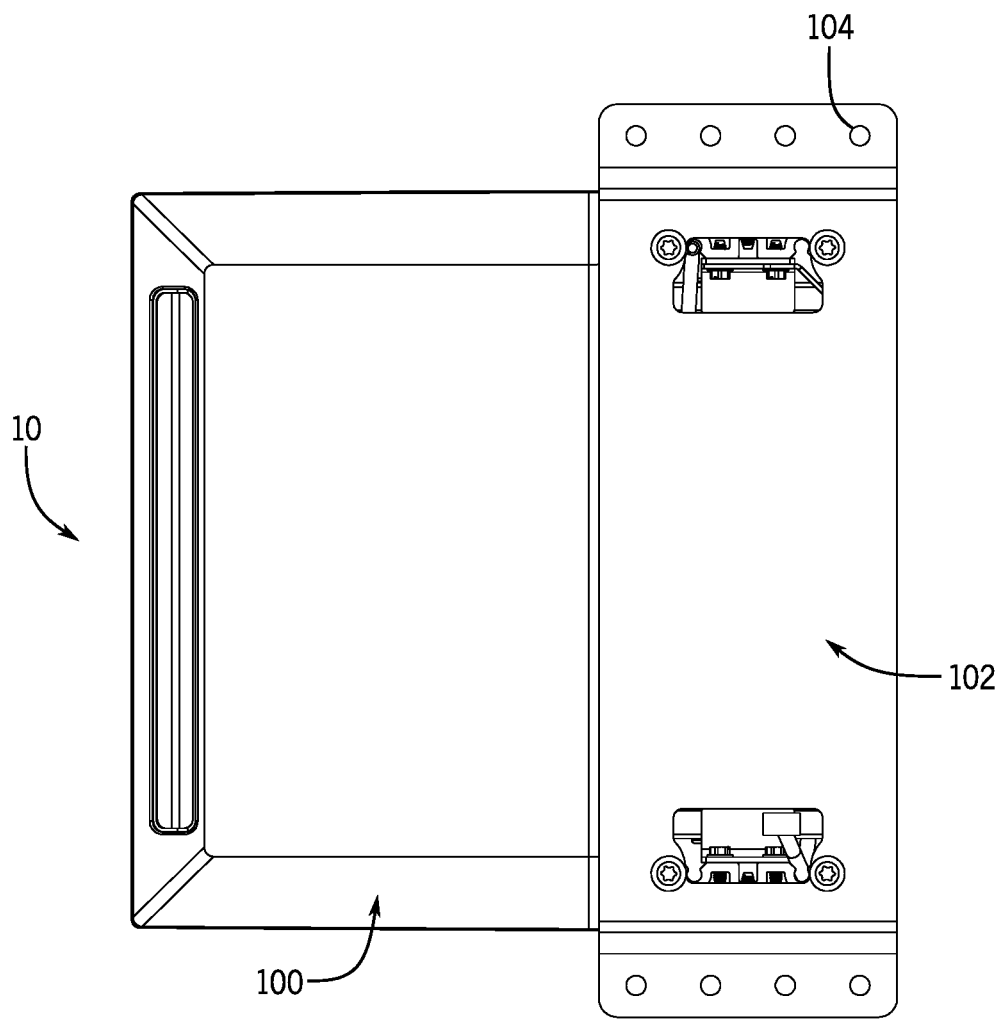
FIG. 4 is a bottom view of the fog generator assembly of FIG. 3.

As shown in FIG. 4, the housing 100 includes a mounting member 102 coupled to a lower end of the housing 100. The mounting member 102 is configured to couple the housing 100 to the support surface. According to an exemplary embodiment, the mounting member 102 is configured as a plate including a plurality of mounting holes 104. The housing 100 is fastened to the support surface using a plurality of mechanical fasteners such as bolts, screws, or any combination thereof. In other exemplary embodiments, the housing 100 is coupled directly to the support surface. In yet other exemplary embodiments, the housing 100 is directly or indirectly coupled to the bath 20.

Figure 5:
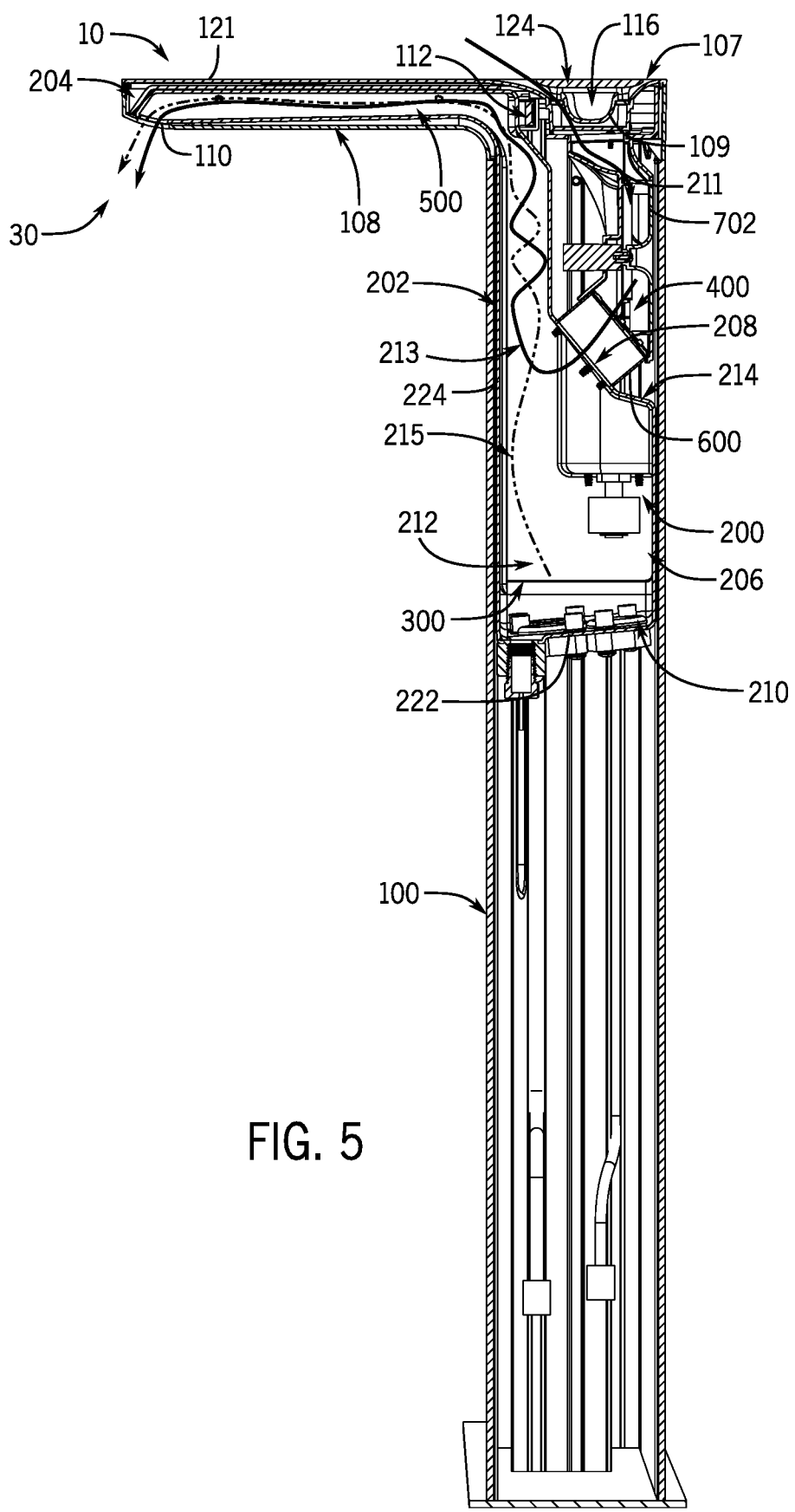
FIG. 5 is a cross-sectional view of the fog generator assembly of FIG. 3, according to an exemplary embodiment.
Figure 6:
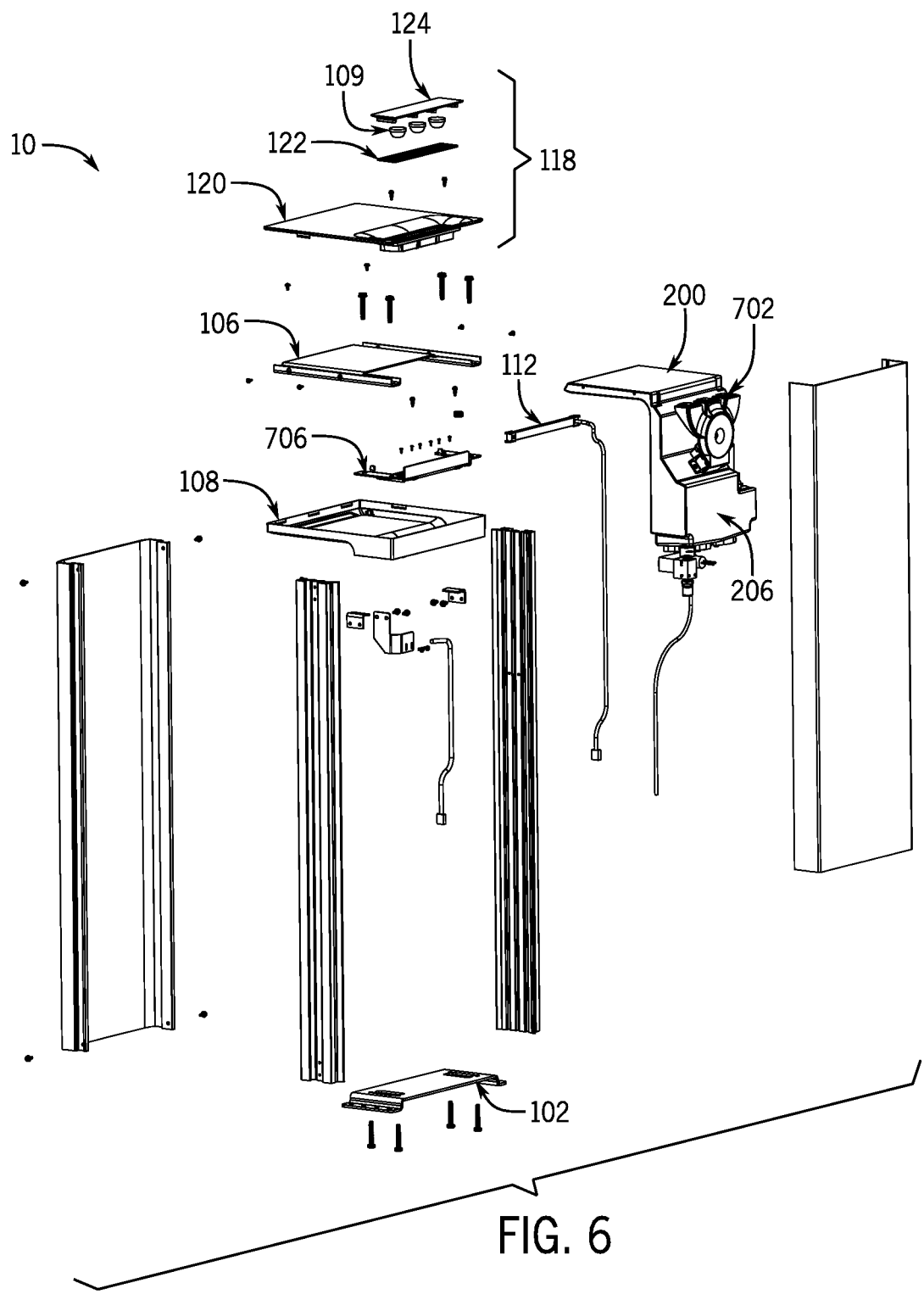
FIG. 6 is an exploded view of the fog generator assembly of FIG. 3, according to an exemplary embodiment.
Figure 13:
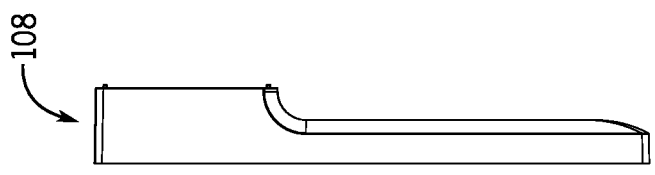
FIG. 13 is a side view of the lower cover of FIG. 11.
Figure 12:
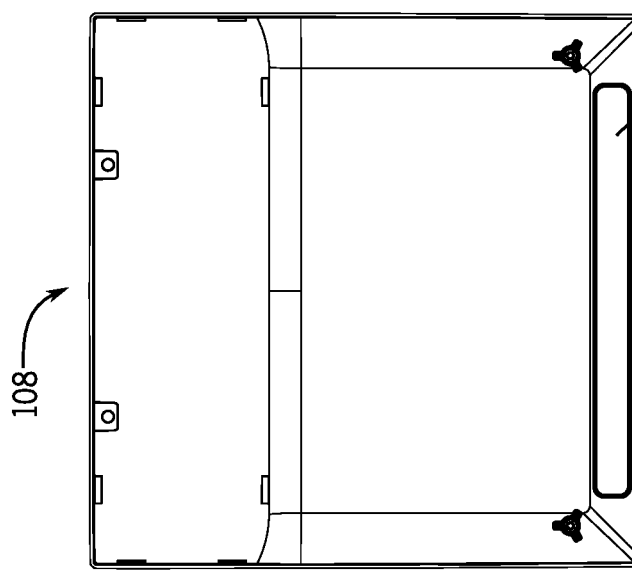
FIG. 12 is a top view of the lower cover of FIG. 11.
Figure 11:
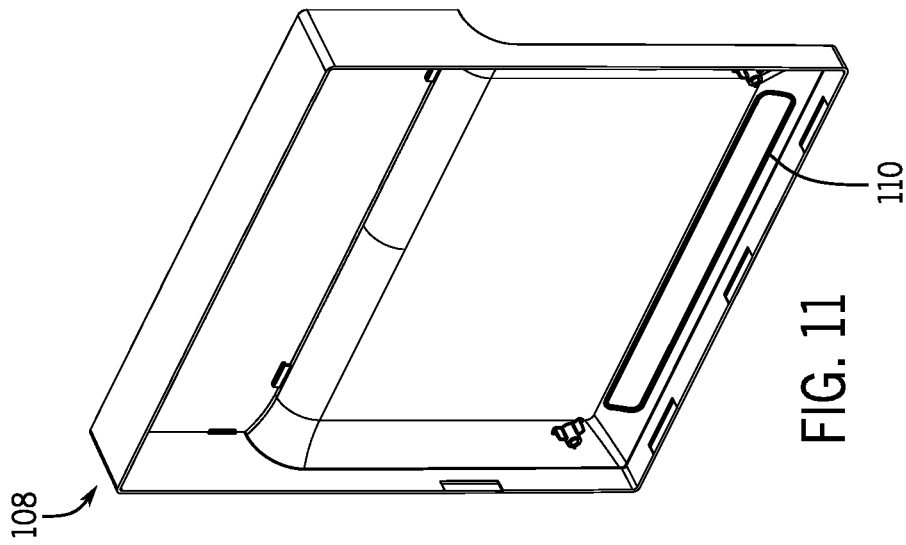
FIG. 11 is a perspective view of a lower cover for the fog generator assembly of FIG. 3, according to an exemplary embodiment.

In the exemplary embodiment show in FIG. 5, the assembly 10 is configured to provide an aromatic fog (e.g., a fragrant mist, etc.) of water vapor 30 to the user occupied space just above the bath 20 (see also FIG. 1). As shown in FIGS. 5-6, the assembly 10 includes a fog generator subassembly 200 configured to produce (e.g., generate, etc.) an aerosolized fog of water vapor and both introduce and mix a fragrance with the fog. In the exemplary embodiment of FIGS. 5-6, the fog generator subassembly 200 is received within the housing 100. A vertical portion 202 of the subassembly 200 is received within the vertical support structure. A horizontal portion 204 of the subassembly 200 is supported by the housing 100 in between an upper bracket 106 and a lower cover 108, which are illustrated in further detail in FIGS. 7-10 and FIGS. 11-13, respectively. As shown in FIGS. 11-13, the lower cover 108 may include a discharge port 110 configured to align with an exit port on the fog generator subassembly 200 (see also FIG. 6).

As shown in FIG. 6, the assembly 10 additionally includes a light source 112 configured to illuminate the discharge port 110 (see also FIG. 5) through which the aromatic fog is ejected. As shown in FIGS. 14-16, the light source 112 may be configured as a light emitting diode (LED) lighting strip, or another compact light source. In an exemplary embodiment, the light source 112 includes a support channel 114 that facilitates mounting of the light source 112 to at least one of the housing 100 and the fog generator subassembly 200. The LED lighting strip may be epoxied or otherwise coupled to the support channel 114. A clip or another suitable fastener may be coupled to a first end and a second end of the support channel 114. The clip may be configured to removably couple the light source 112 to at least one of the housing 100 and the fog generator subassembly 200. The light source 112 may be directed through a discharge portion of the fog generator subassembly 200, or alternatively through a portion of the housing 100 outside of the fog generator subassembly 200. In the exemplary embodiment shown in FIGS. 7-10, the upper bracket 106 includes a forward lip 115 configured to reflect light from the light source 112 toward the discharge port 110. In this manner, light from the light source 112 can be more uniformly distributed outward from the discharge port 110 and along a length of the discharge port 110, which can, advantageously, appear to the user as a stream of light passing through the discharge port 110.

Referring to FIG. 5, the fog generator subassembly 200 includes a fog generating portion 300 (e.g., a water vapor generator), an aromatic dispensing portion 400 (e.g., a fragrance dispenser) fluidly coupled to the fog generating portion 300, and a mixing portion 500 (e.g., a mixing element) fluidly coupled to both the fog generating portion 300 and the aromatic dispensing portion 400. According to an exemplary embodiment, the aromatic dispensing portion 400 is also fluidly coupled to a space surrounding the assembly 10 (e.g., the surroundings, a space within the bathroom environment, etc.), and the mixing portion 500 is fluidly coupled to the user occupied space. The assembly 10 includes an air displacement device, shown as fan 600, configured to move air through each portion 300, 400, 500 of the fog generator subassembly 200. In the exemplary embodiment of FIGS. 5-6, the fan 600 is disposed on a housing of the fog generator subassembly 200, shown as fog tank 206, proximate to an intersection between each of the fog generating portion 300, aromatic dispensing portion 400, and mixing portion 500. Air 211 is pulled through the fan 600 from the aromatic dispensing portion 400 toward the fog generating and mixing portions 300, 500. Air 211 is received from the space surrounding the assembly 10 into the housing 100 through an aperture 107 disposed on an upper surface of the housing 100. Air 211 proceeds through one or more chambers 116 where it is exposed to one, or a combination of, aromatic liquids. The fragrance 213 is carried by air 211 passing through the activated chamber. The fragrance 213 moves with the air 211 into a flow control manifold 702 and out through an upper opening 208 in the fog tank 206 (e.g., an upper opening 208 fluidly coupled to both the fog generating portion 300 and the mixing portion 500, etc.). Proximate to the upper opening 208, the fragrance 213 is introduced to an aerosolized fog of water vapor 215, which is generated in a cavity 212 of the fog generating portion 300. Among other benefits, mixing the fragrance 213 with the fog of water vapor 215 stimulates multiple user senses (i.e., is multi-sensory) and contributes to an enhanced bathing experience; the fragrance 213 stimulating a user's sense of smell and the fog 215 stimulating both a user's sense of sight and touch (e.g., a cooling effect provided to the user via a wetting of the user's skin, the cooling of the user by a fog of water vapor at a different temperature than the user, etc.). The fragrance 213 continues to mix with the water vapor 215 throughout the mixing portion 500, from which the aromatic fog is ultimately ejected to the user occupied space.

Figure 17:
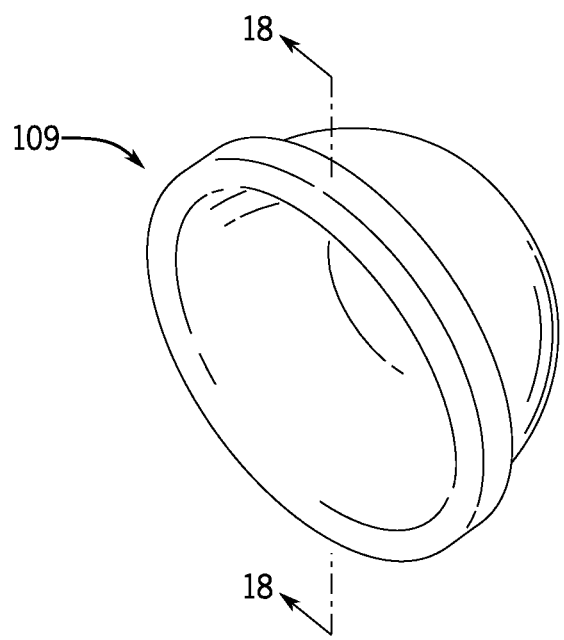
FIG. 17 is a perspective view of a removable well for the fog generator assembly of FIG. 3, according to an exemplary embodiment.
Figure 18:
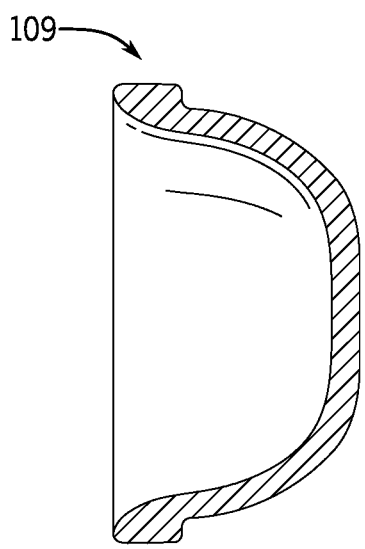
FIG. 18 is a side view of the well of FIG. 17.
Figure 19:
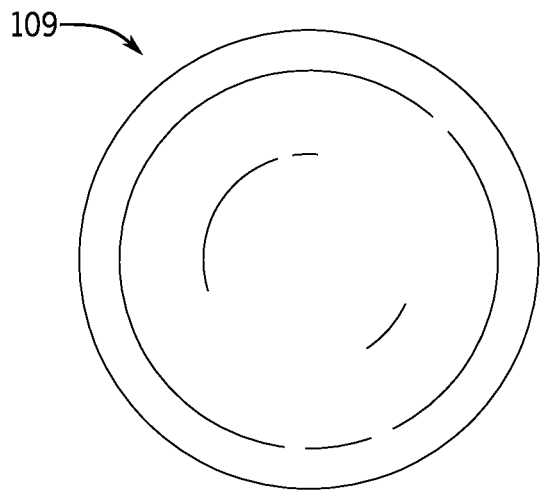
FIG. 19 is a top view of the well of FIG. 17.
Figure 20:
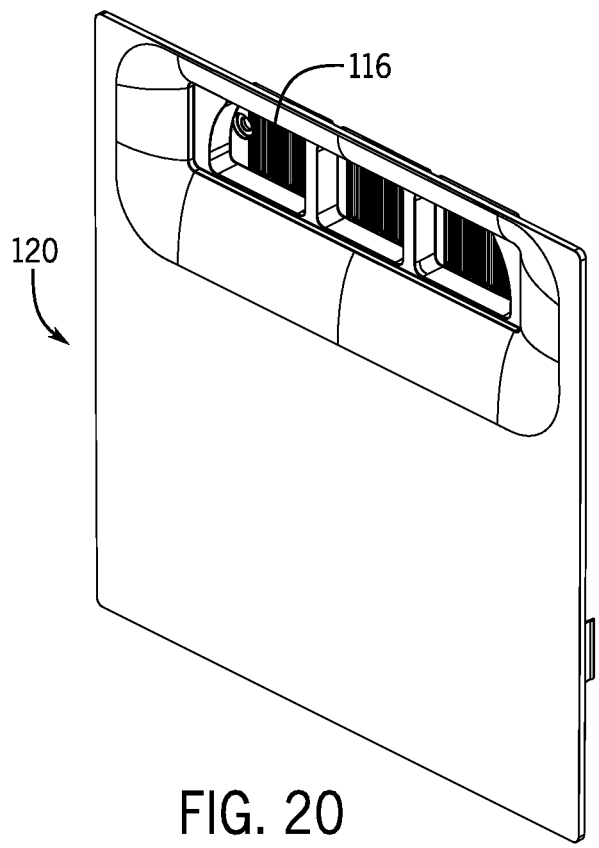
FIG. 20 is a perspective view of a support shelf for the fog generator assembly of FIG. 3, according to an exemplary embodiment.
Figure 22:
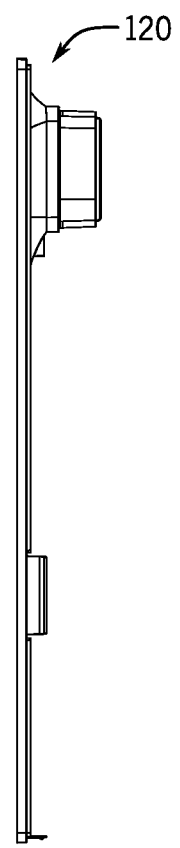
FIG. 22 is a side view of the support shelf of FIG. 20.
Figure 21:
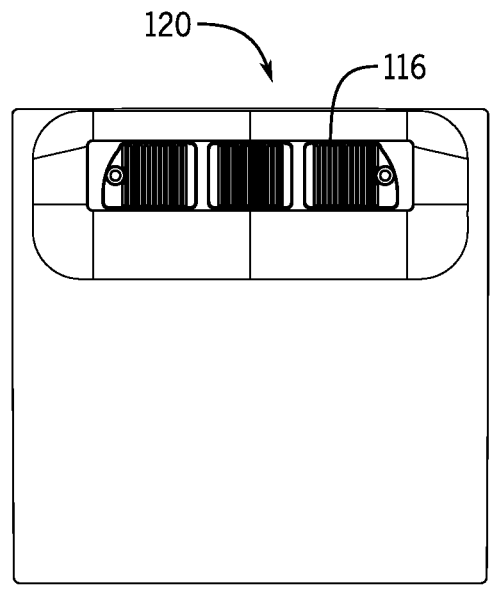
FIG. 21 is a top view of the support shelf of FIG. 20.
Figure 23:
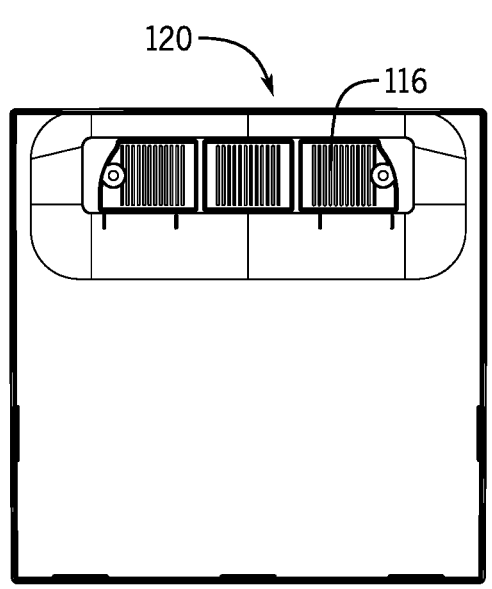
FIG. 23 is a bottom view of the support shelf of FIG. 20.
Figure 24:
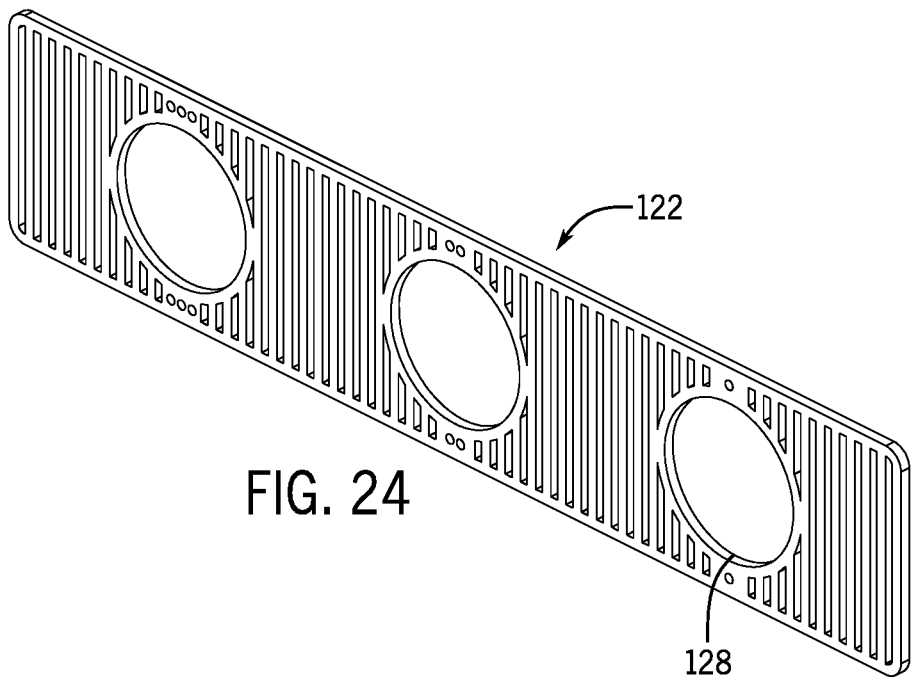
FIG. 24 is an isometric view of a well support for the fog generator assembly of FIG. 3, according to an exemplary embodiment.
Figure 25:
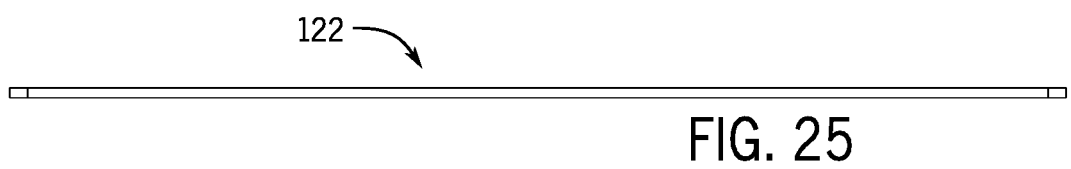
FIG. 25 is a front view of the well support of FIG. 24.
Figure 26:
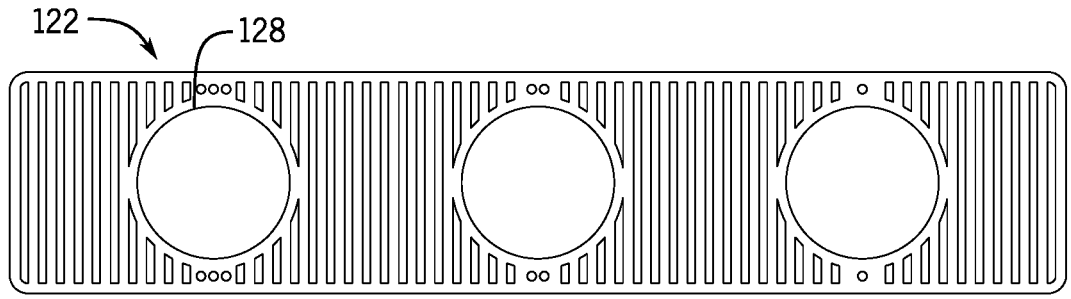
FIG. 26 is a top view of the well support of FIG. 24.
Figure 27:
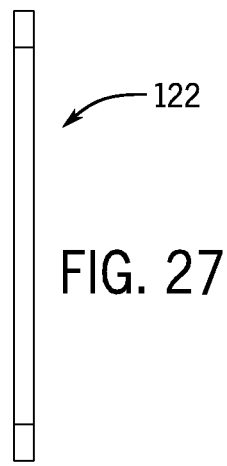
FIG. 27 is a side view of the well support of FIG. 24.
Figure 28:
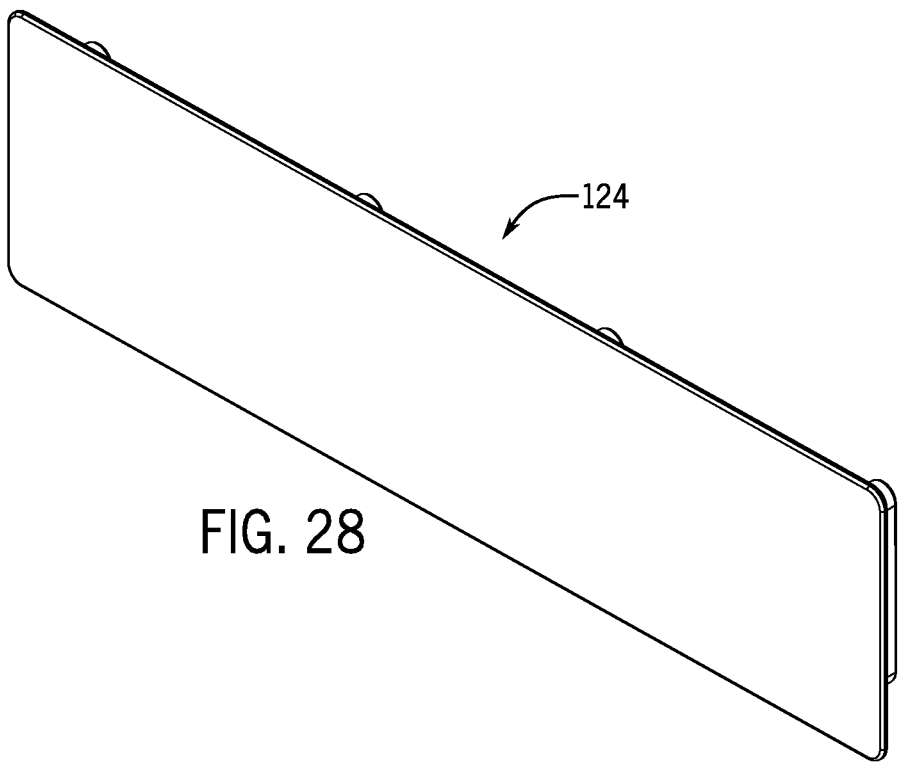
FIG. 28 is an isometric view of a chamber cover for the fog generator assembly of FIG. 3, according to an exemplary embodiment.
Figure 29:
FIG. 29 is a front view of the chamber cover of FIG. 28.
Figure 30:
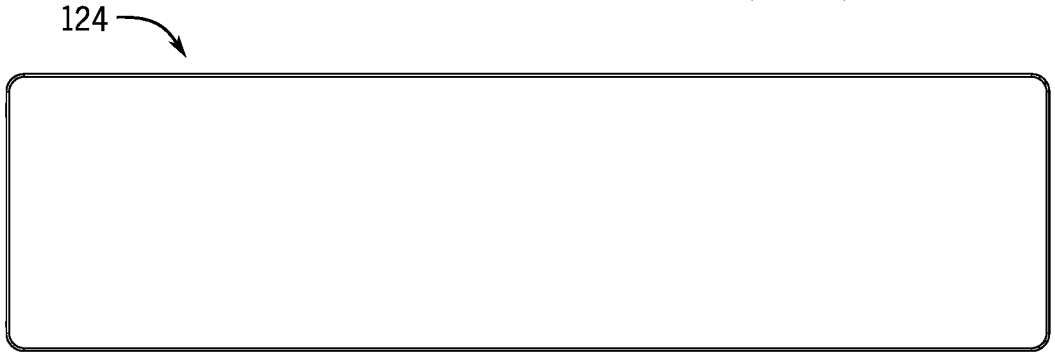
FIG. 30 is a top view of the chamber cover of FIG. 28.
Figure 31:
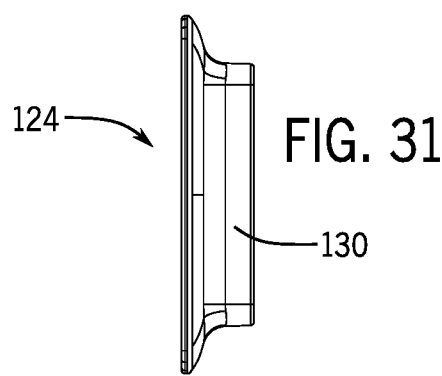
FIG. 31 is a side view of the chamber cover of FIG. 28.

In the exemplary embodiment shown in FIGS. 17-19, the aromatic liquids are provided in the form of essential oils contained within a plurality of individual wells 109. The essential oils may emit any one of a plurality of different fragrances (e.g., lavender, vanilla, eucalyptus, peppermint, etc.). The wells 109 may be refillable and removable from the assembly 10 to facilitate replenishment of oils and/or replacement of damaged wells 109.

An exemplary embodiment of a well support assembly 118 is shown in FIG. 6. The well support assembly 118 includes a support shelf 120, a well support 122, and a chamber cover 124. As shown in FIG. 6, the support shelf 120 is coupled to the lower cover 108 and forms a substantially planar top surface 121 of the assembly 10. Among other benefits, the proximity of the top surface 121 to a user of the bath 20 provides an easily accessible dry space to support sensitive electronics (e.g., a mobile phone, watch, etc.). In the exemplary embodiment shown in FIGS. 20-23, each of the one or more chambers 116 is disposed in the support shelf 120. The chambers 116 are formed as a plurality of recessed areas toward a rear edge of the support shelf 120. As shown in FIGS. 24-27, each of the wells 109 is supported within the chamber 116 by a well support 122 (i.e., an edge of the support shelf 120 that is farthest from the bath 20 of FIG. 1) (see also FIG. 17). The well support 122 is configured as a substantially rectangular plate with through holes 128 disposed at approximately equally spaced intervals along a length of the plate, although other spacing is contemplated. Each of the holes 128 is configured to receive one of the wells 109. The wells 109 are supported by the well support 122 along an upper ledge of the well 109 (see also FIGS. 17-19). In the exemplary embodiment of FIGS. 24-27, each chamber 116 is configured to accommodate a single well 109 (See also FIG. 17). In other exemplary embodiments, each chamber 116 may be configured to accommodate multiple wells 109. According to an exemplary embodiment, both the well support 122 and the support shelf 120 may include a perforated portion to allow the air to move freely through the aromatic dispensing portion 400.

As shown in FIG. 5, a chamber 116 containing one or more wells 109 of the plurality of wells 109 is fluidly coupled to both the fog generating and mixing portions 300, 500 by a flow control manifold 702. According to an exemplary embodiment, the flow control manifold 702 is configured to facilitate the delivery of a fragrance from one or more chambers 116. Each of the one or more chambers 116 is at least partially fluidly isolated from the other chambers 116 by the chamber cover 124, so as to prevent scents from one well 109 from altering (e.g., contaminating, mixing with, polluting, etc.) the scents from wells 109 in adjacent chambers 116. An exemplary embodiment of the chamber cover 124 is shown in FIGS. 28-31. The chamber cover 124 includes a plurality of protrusions 130 that form a partition between adjacent chambers 116. The protrusions 130 may, advantageously, engage with the support shelf 120 or well support 122 to help to align the chamber cover 124 with the recessed areas of the well support 122. The protrusions 130 also space the chamber cover 124 a distance vertically from the top of the wells 109 so as to allow space for air to be pulled into the aromatic dispensing portion 400 (see also FIG. 5). In other exemplary embodiments, the chamber cover 124 is retractable onto an upper surface of the wells 109. Utilizing a retractable chamber cover 124 can, advantageously, reduce evaporation from the wells 109 in one or more of the chambers 116 during periods of non-use.

Figure 32:
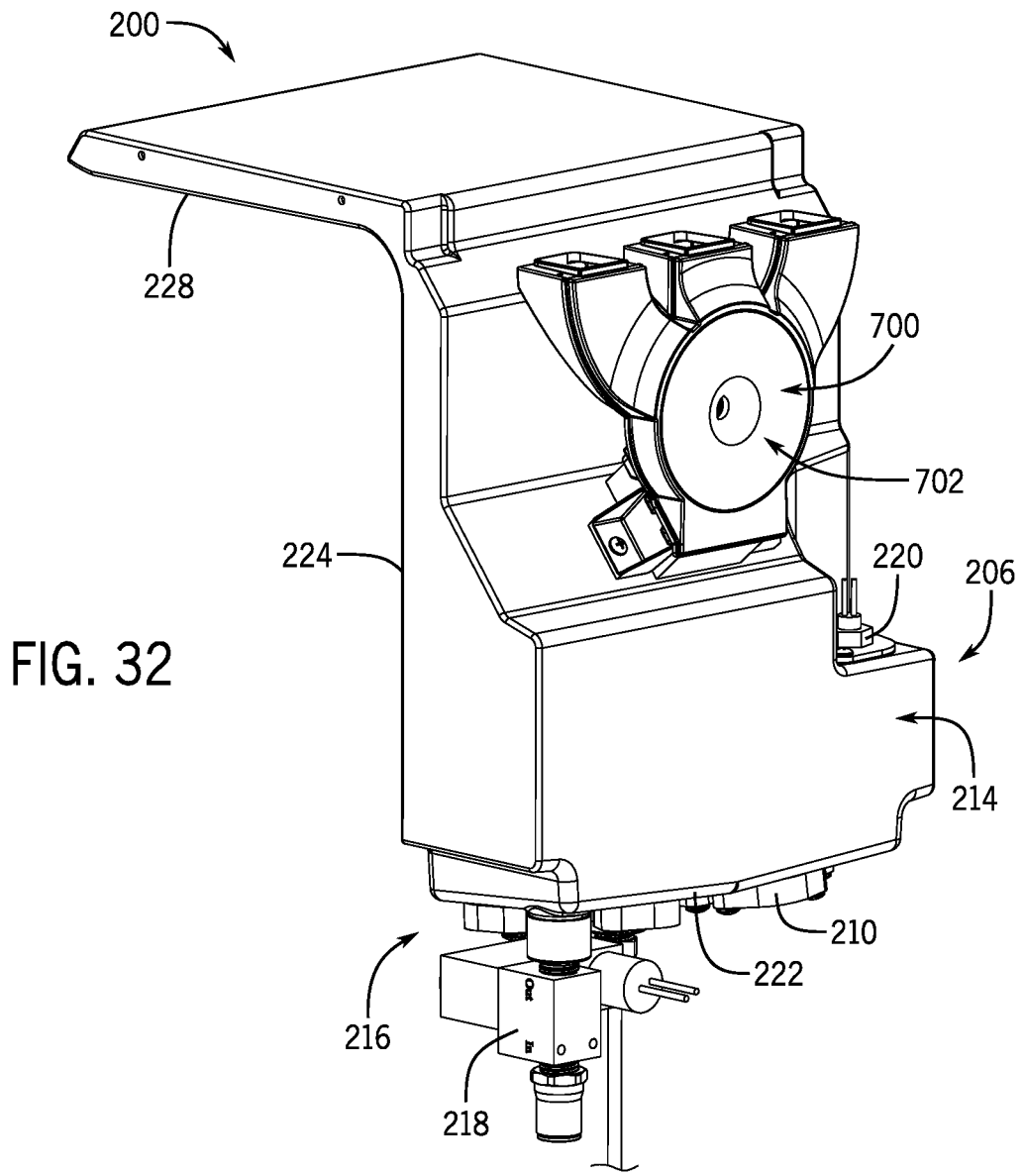
FIG. 32 is a perspective view of a fog generator subassembly for the fog generator assembly of FIG. 3, according to an exemplary embodiment.
Figure 33:
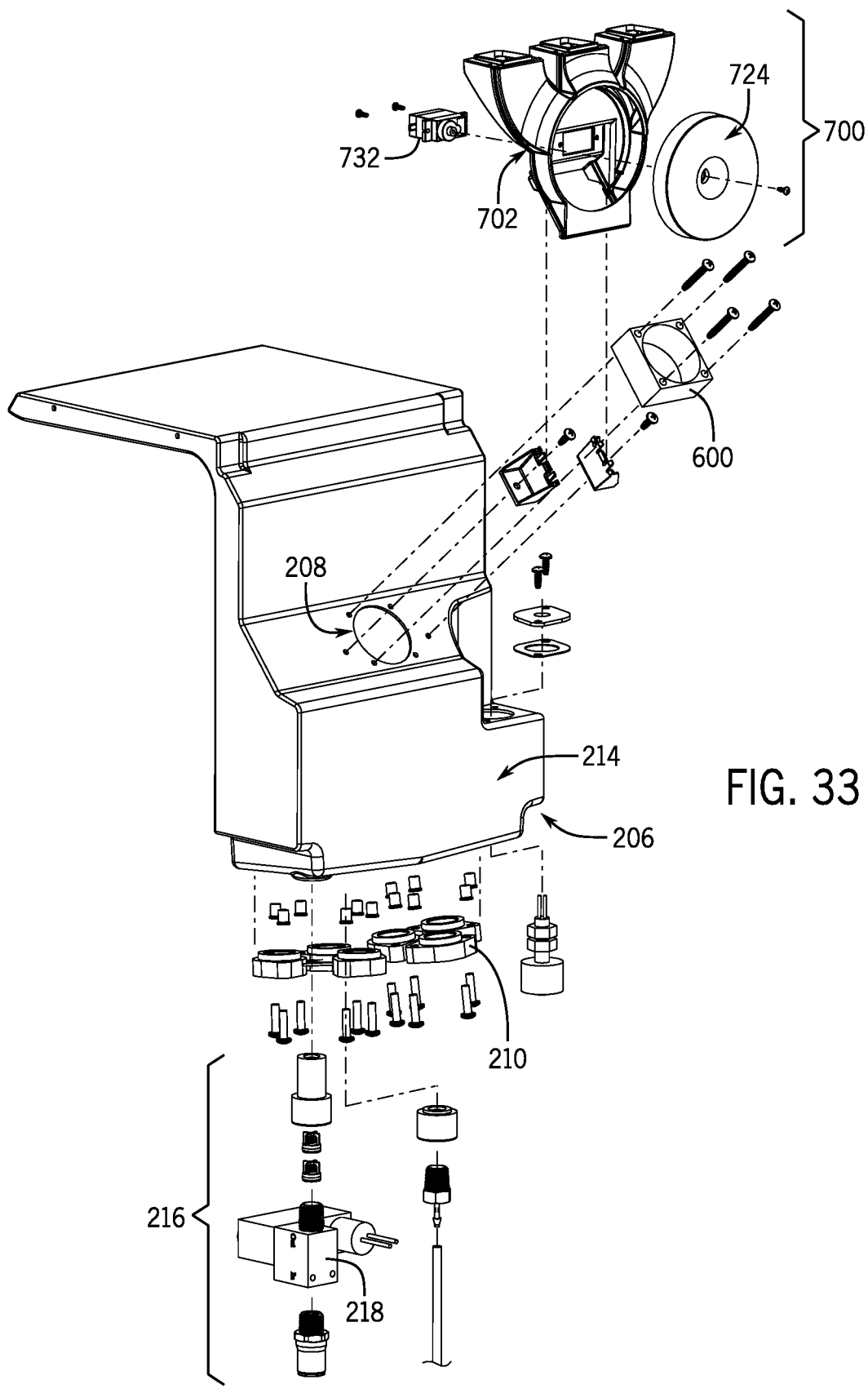
FIG. 33 is an exploded view of the fog generator subassembly of FIG. 32, according to an exemplary embodiment.
Figure 48:
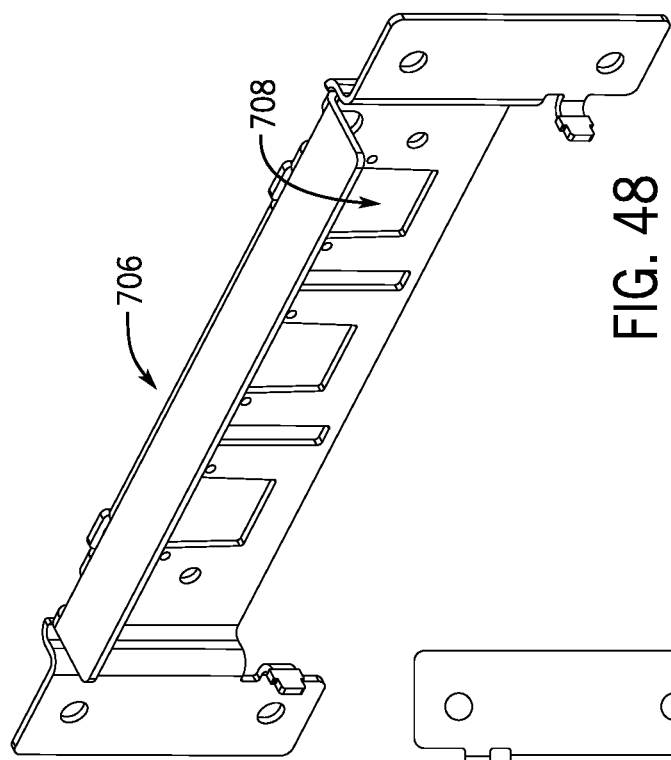
FIG. 48 is a perspective view of a manifold bracket for the fog generator subassembly of FIG. 32, according to an exemplary embodiment.
Figure 51:
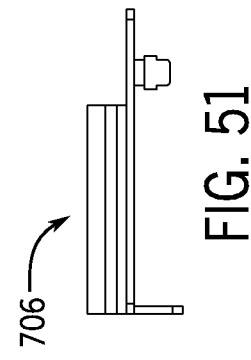
FIG. 51 is a side view of the manifold bracket of FIG. 48.
Figure 49:
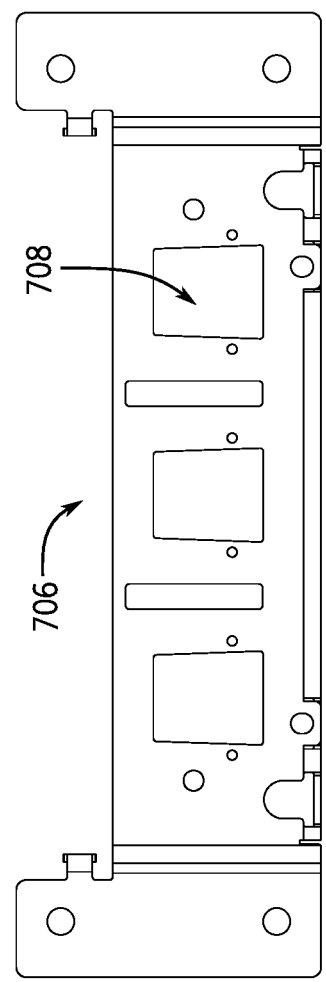
FIG. 49 is a top view of the manifold bracket of FIG. 48.
Figure 50:
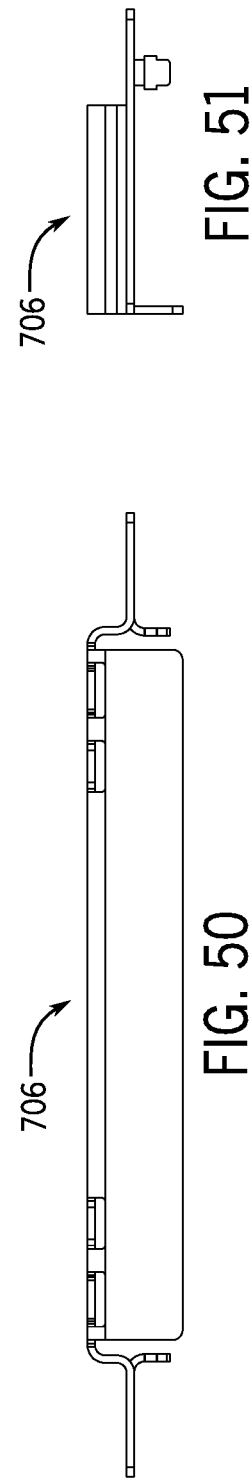
FIG. 50 is a front view of the manifold bracket of FIG. 48.

FIGS. 32-33 show the fog generator subassembly 200 separated from the assembly 10, according to an exemplary embodiment. As shown in FIGS. 32-33, the fog generator subassembly 200 includes a fog tank 206 and a flow control manifold 702 coupled thereto. The fog generator subassembly 200 is configured to produce an aerosolized mist of water vapor using one or more ultrasonic devices 210 (e.g., ultrasonic nebulizers, etc.). As shown in FIGS. 34-35, the fog generator subassembly 200 includes a cavity 212 (e.g., reservoir, etc.) defined by an outer wall 214 of the fog tank 206. The cavity 212 is disposed below (i.e., downwardly from) the upper opening 208 of the fog tank 206. The cavity 212 is configured to hold a volume of liquid within the fog tank 206. As shown in FIGS. 34-35, the fog generator subassembly 200 includes a water delivery and metering system 216 configured to fill the cavity 212 with water as well as control a height (i.e., a volume) of the water within the cavity 212. In an exemplary embodiment, the water delivery and metering system 216 includes a water supply line configured to fluidly couple the cavity 212 with a water source (e.g., a household water supply, etc.) and a water drain line configured to fluidly couple the cavity 212 with a drain (e.g., a floor drain, a household sewer/waste line, etc.). The supply and drain lines may be coupled to the fog tank 206 using a water-tight fastening mechanism such as a barbed fitting, a compression tube fitting such as a Swagelok fitting, or any combination thereof. The inlet fitting may include one or more check valves configured to prevent backflow of water from the fog tank 206 into the water source.

In the exemplary embodiment of FIGS. 34-35, the water delivery and metering system 216 includes a flow control valve 218 (e.g., a solenoid valve, etc.) and a fluid level measurement sensor 220 (e.g., a float sensor, etc.) communicatively coupled thereto. Together, the flow control valve 218 and the level measurement sensor 220 are configured to control the level (e.g., the volume) of water contained within the cavity 212. In an exemplary embodiment, the flow control valve 218 is configured to fluidly couple to the cavity 212 to the water supply line until the level of water is just below the level of the upper opening 208 of the fog tank 206. Among other benefits, raising the upper opening 208 above the waterline prevents liquid water from sealing off the upper opening 208 and/or restricting flow of the fragrance into the cavity 212 through the upper opening 208. In an exemplary embodiment, the flow control valve 218 and level measurement sensor 220 may be integrally formed (e.g., an integral float actuator).

According to the exemplary embodiment of FIGS. 34-35, the water delivery and metering system 216 is configured to continuously drain water from the cavity 212, which can, advantageously, prevent the growth of bacteria in the cavity 212 and other parts of the fog generator subassembly 200 during periods of non-use. According to an exemplary embodiment, the cavity 212 is at least partially defined by a lower wall 222 enclosing the bottom of the cavity 212. The lower wall 222 is formed at an angle to prevent water from pooling or from otherwise being captured (e.g., retained, etc.) within the fog tank 206. As shown in FIGS. 34-35, the drain is disposed at a lowest point (vertically) along the lower wall 222. In an exemplary embodiment, the lowest point is disposed centrally, proximate to a forward wall 224 of the fog tank 206. Note that, in an exemplary embodiment, there are no horizontal surfaces or angled surfaces within the fog tank 206 upon which water could accumulate, thereby helping to reduce the chances for bacteria growth. As shown in FIG. 34, the fog tank 206 includes a substantially horizontal portion 204 configured to direct (e.g., channel, guide, etc.) the aromatic fog of water vapor toward the user occupied space. A base wall 228 (i.e. a bottom wall, etc.) of the horizontal portion 204 is angled toward an exit port of the fog tank 206 to ensure any condensation remaining on the base wall 228 can discharge through the exit port.

As shown in FIGS. 34-35, the fog generator subassembly 200 additionally includes a plurality of ultrasonic devices 210 configured to agitate the water contained within the cavity 212. Each of the ultrasonic devices is disposed in the fog tank 206 along the lower wall 222. In the embodiment of FIGS. 34-35, the fog generator subassembly 200 includes six ultrasonic devices 210, although more or fewer ultrasonic devices 210 may be used in other exemplary embodiments. According to an exemplary embodiment, the ultrasonic devices 210 take the form of high frequency nebulizers (e.g., 1.65 MHz nebulizers or another suitable oscillating frequency). As shown in FIGS. 36-39, the fog tank 206 includes a plurality of countersunk openings 230 disposed in the lower wall 222, each of the countersunk openings 230 is configured to receive a corresponding one of the ultrasonic devices 210 (see also FIG. 35). In an exemplary embodiment, the ultrasonic devices 210 are coupled to the lower wall 222 of the fog tank 206 using threaded inserts that are molded, heat set, pressed, or otherwise formed into the lower wall 222. A grommet, O-ring, or another water-tight sealing mechanism may be pressed into a recessed portion of each of the countersunk openings 230 to prevent water from leaking from the fog tank 206.

The design of the fog tank 206 described with reference to FIGS. 32-39 should not be considered limiting. Many alternatives are possible without departing from the inventive concepts disclosed herein. For example, FIGS. 40-42 show a fog tank 250 that utilizes a separate, self-contained ultrasonic fogger device 252 as opposed to individual ultrasonic devices (e.g., nebulizers). The fog tank 250 includes a housing 254 that is formed in two pieces, an upper portion 256 and a lower portion 258. During assembly, the self-contained ultrasonic fogger device 252 is placed into the lower portion 258 of the housing 254. The lower portion 258 includes a plurality of standoffs 260 that extend upwardly from a lower wall 262 of the lower portion 258 that engage with the fogger device 252 to space the fogger device 252 a distance from the lower wall 262 (e.g., to form a gap between the lower wall 262 and the fogger device 252). Among other benefits, the spacing between the fogger device 252 and the lower wall 262 allows water to flow freely along the lower wall 262 to a drain 264 disposed in the lower wall 262. Like the fog tank 206 of FIGS. 32-39, the lower wall 262 of the fog tank 250 of FIGS. 40-42 is sloped (e.g., angled, curved, etc.) toward the drain 264 to prevent water from pooling within the housing 254 during periods of non-use. The lower portion 258 is ultrasonically welded or otherwise coupled to the upper portion 256 to provide a water-tight seal between a cavity 266 defined by the housing 254 and an environment surrounding the fog tank 250.

According to an exemplary embodiment shown in FIG. 43, the fog generator subassembly 200 includes an aromatic sequence control system 700. The sequence control system 700 includes a flow control manifold 702 configured to guide (e.g., direct, channel, etc.) a fragrance (i.e., fragrant air, etc.) from one or more chambers 116 (see also FIG. 20) in the support shelf 120 through the upper opening 208 in the fog tank 206 (see also FIGS. 32-33). In the exemplary embodiment shown FIGS. 44-47, the flow control manifold 702 is formed from two pieces of material (e.g., plastic, etc.) that are welded, glued, or snapped, or otherwise coupled together. In other exemplary embodiments, the flow control manifold 702 may be formed as a single unitary piece. As shown in FIG. 43, a first end 704 of the flow control manifold 702 is coupled to the manifold bracket 706, which is further coupled to the support shelf 120. In the exemplary embodiment shown in FIGS. 48-51, the manifold bracket 706 includes a plurality of ports 708 through which air may pass. The manifold bracket 706 includes additional holes, slots, and retaining features configured to facilitate integration of the various components into the assembly 10 (see also FIGS. 5-6).

Figure 7:
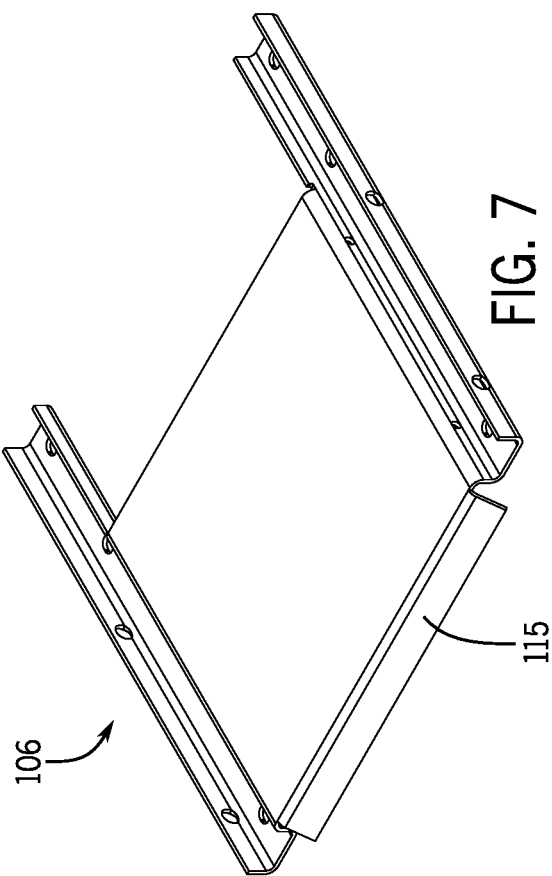
FIG. 7 is a perspective view of an upper bracket for the fog generator assembly of FIG. 3, according to an exemplary embodiment.
Figure 10:
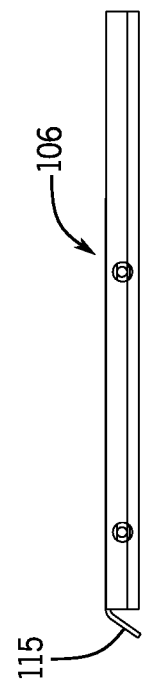
FIG. 10 is a side view of the upper bracket of FIG. 7.
Figure 8:
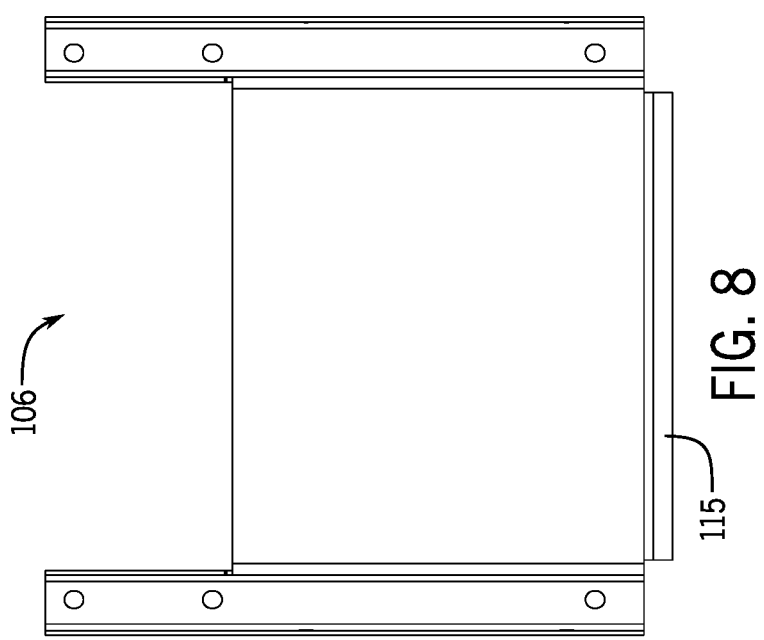
FIG. 8 is a top view of the upper bracket of FIG. 7.
Figure 9:
FIG. 9 is a front view of the upper bracket of FIG. 7.

Returning to FIGS. 44-47, the first end 704 of the flow control manifold 702 includes a plurality of inlet channels, shown as first inlet channel 710, second inlet channel 712, and third inlet channel 714. Each of the inlet channels 710, 712, 714 is fluidly coupled to a corresponding one of the chambers 116 in the support shelf 120. A second end 716 of the flow control manifold 702 is coupled to the fog tank 206 (e.g., indirectly or directly coupled to the fog tank 206, coupled to the fog tank 206 by a fan adapter bracket, etc.). As shown in FIGS. 44-7, the second end 716 of the flow control manifold 702 includes a discharge channel 718 that is fluidly coupled to the upper opening 208 in the fog tank 206, and correspondingly, the cavity 212.

In the exemplary embodiment of FIGS. 44-47, the channels 710, 712, 714, 718 are arranged around a central valve cavity 720. The walls of each of the inlet channels 710, 712, 714 define a central axis 722 for each of the inlet channels 710, 712, 714. As shown in FIG. 43, the central axes 722, 723, 725 are separated from one another by approximately 60°, although the angular spacing between adjacent inlet channels 710, 712, 714 may be different in other exemplary embodiments.

Figure 52:
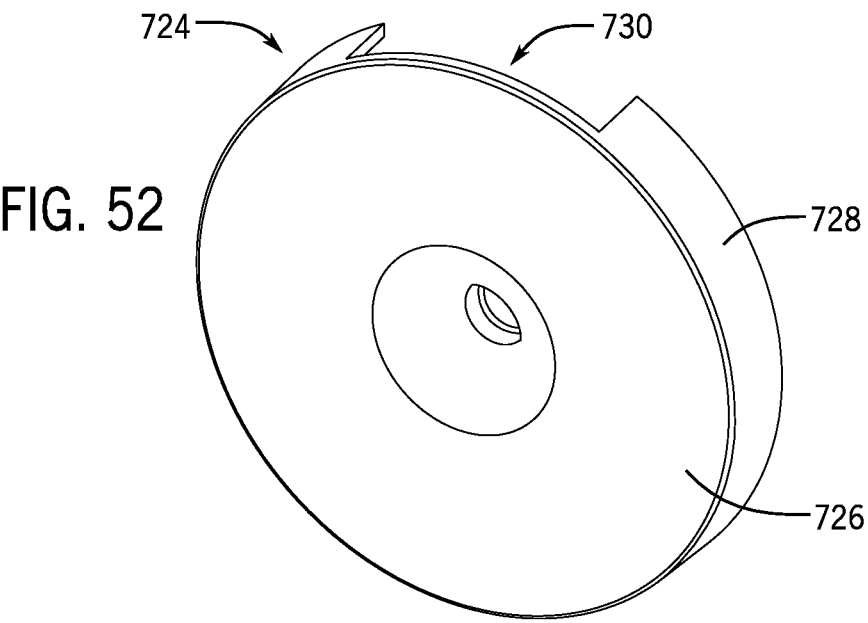
FIG. 52 is a perspective view of a manifold valve member for the fog generator subassembly of FIG. 32.
Figure 53:
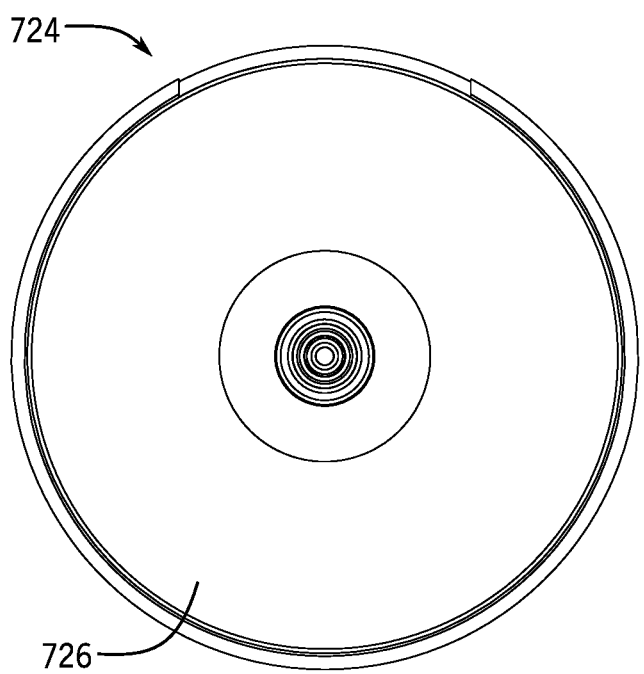
FIG. 53 is a front view of the valve member of FIG. 51.
Figure 54:
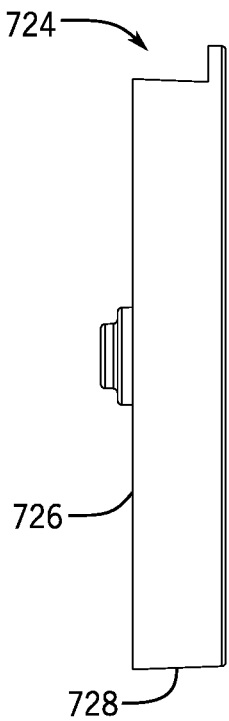
FIG. 54 is a side view of the valve member of FIG. 51.

The valve cavity 720 is dimensioned to receive a substantially cylindrical manifold valve member, shown as valve member 724 in the exemplary embodiment of FIGS. 52-54. As shown in FIGS. 52-54, the valve member 724 is configured as a disk that includes a central wall 726 and an outer wall 728 extending therefrom. The outer wall 728 extends along an outer perimeter of the central wall 726 in a direction that is substantially perpendicular to the central wall 726. Together, the central wall 726 and the outer wall 728 define a hollow portion configured substantially in the shape of a cup. A slot 730 is disposed through the outer wall 728 of the valve member 724. As shown in FIG. 43, the slot 730 can be aligned with any one of the inlet channels 710, 712, 714. In the exemplary embodiment of FIG. 43, an angular extent of the slot 730 is approximately equal to an angular extent of one of the inlet channels 710, 712, 714.

The valve member 724 is configured to selectively control the flow of air through each of the chambers 116 in the support shelf 120. The flow of air through any individual chamber 116 is activated by rotating the valve member 724 such that the slot 730 is at least partially aligned with the inlet channel 710, 712, 714 that is fluidly coupled to the desired chamber 116. In the embodiment of FIG. 43, the valve member 724 is configured to fluidly couple the third inlet channel 714 with the upper opening 208 of the fog tank 206. In an exemplary embodiment, the valve member 724 is configured to rotate in approximately 30° increments between each of the inlet channels 710, 712, 714, although other angular increments may be used. By way of example, rotating the valve member 724 in a counterclockwise direction by approximately 30° from the orientation shown in FIG. 43 at least partially opens the second inlet channel 712, such that air may pass simultaneously through both the second inlet channel 712 and the third inlet channel 714. Rotating the valve member 724 by another 30° (i.e. a total angular rotation of approximately 60° from the initial positon shown in FIG. 43) fully opens the second inlet channel 712 while preventing the flow of air through the first inlet channel 710 and third inlet channel 714. In this manner, various combinations of aromatics and aromatic control sequences are achievable.

In the exemplary embodiment of FIG. 43, the aromatic sequence control system 700 includes an actuator, shown as rotary actuator 732. The rotary actuator 732 is coupled to, and supported by, the flow control manifold 702. The rotary actuator 732 is rotatably coupled to the valve member 724 and configured to control a position of the rotary actuator 732. The rotary actuator 732 includes an extension member that engages with the valve member 724 proximate to a primary axis of the valve member 724. In an exemplary embodiment, the rotary actuator 732 is a multi-position servo actuator.

The control system 700 may additionally include control electronics communicatively coupled to the rotary actuator 732, fan 600, ultrasonic device 210, and valve member 724. The control system 700 may include a processor, memory, and a network communications interface. The network communications interface may be configured, in part, to receive a wireless signal (e.g., Bluetooth, WiFi, etc.) from a remote device (e.g., a control device, etc.).

Figure 55:
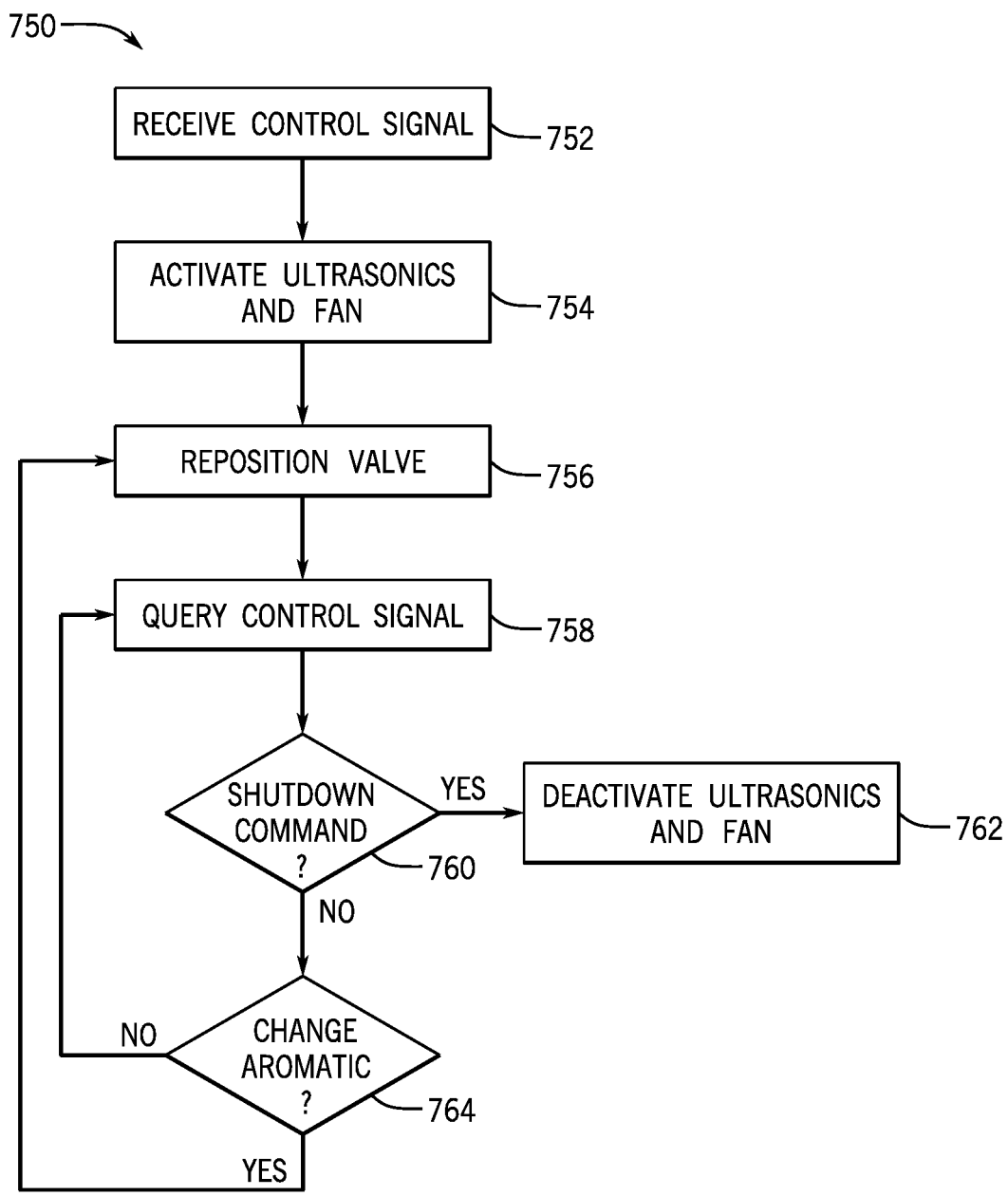
FIG. 55 is a schematic illustration of a method of control for a fog generator assembly, according to an exemplary embodiment.
Figure 56:
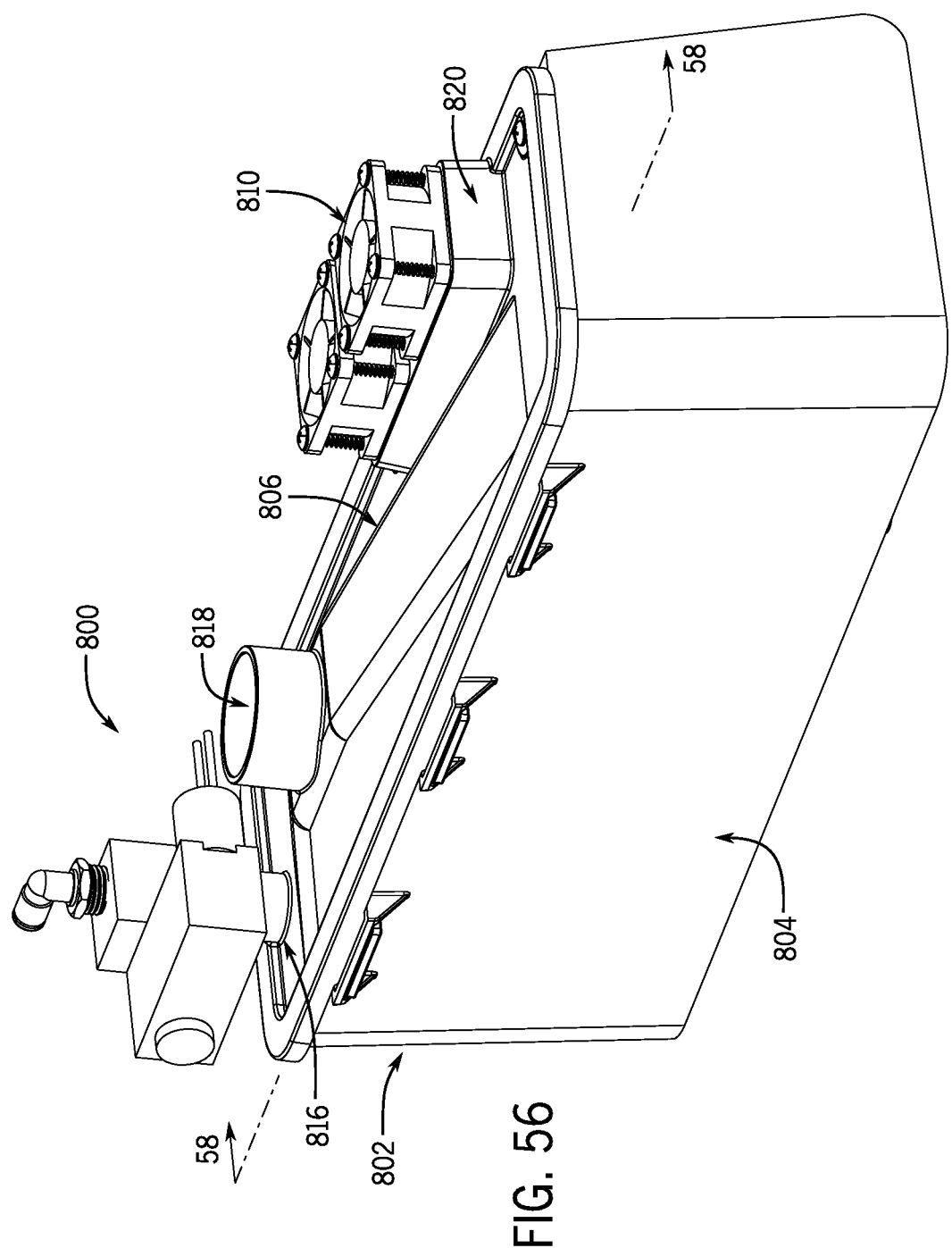
FIG. 56 is a front perspective view of a fog generator assembly, according to another exemplary embodiment.
Figure 57:
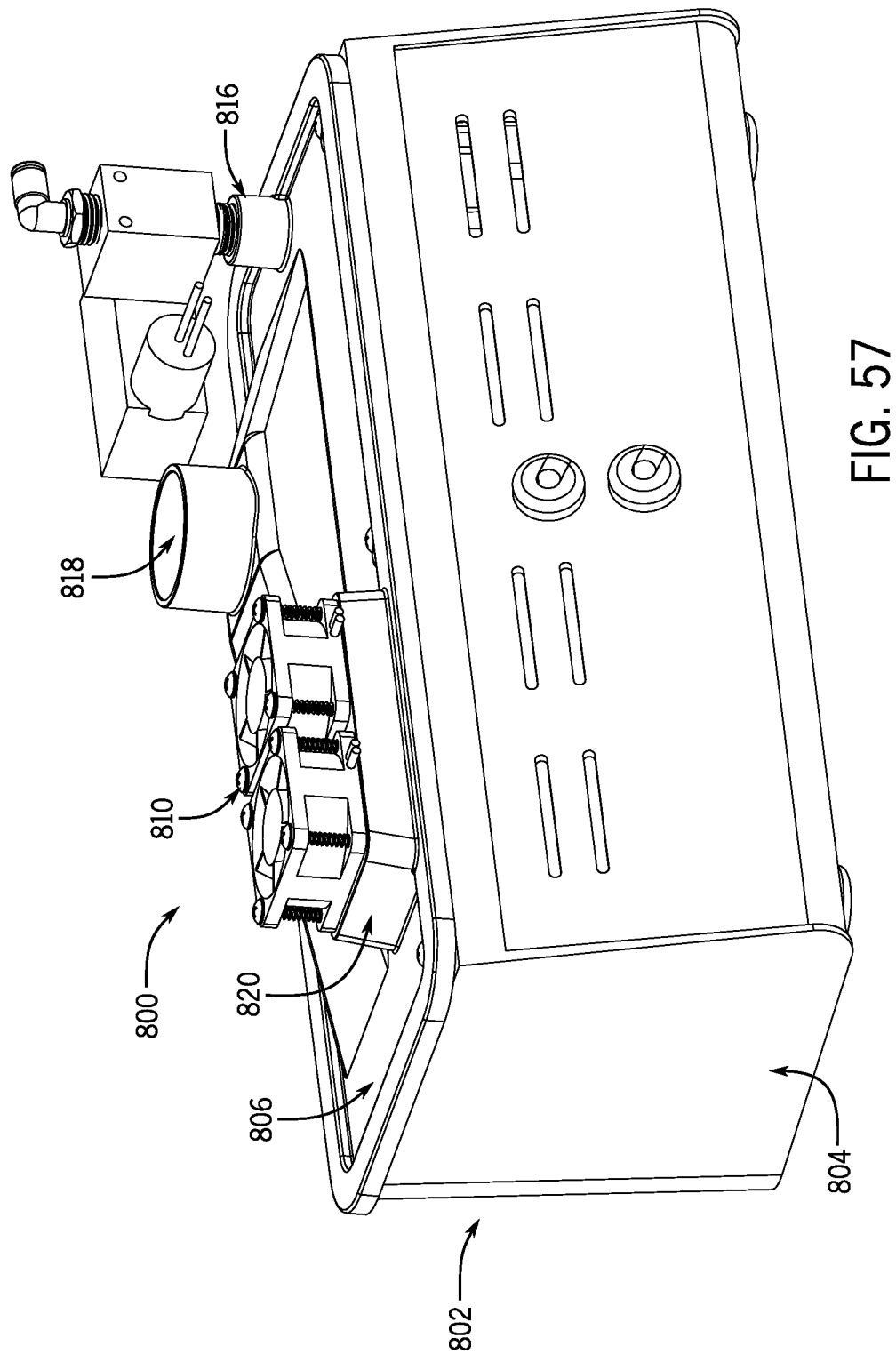
FIG. 57 is a back perspective view of the fog generator assembly of FIG. 56.
Figure 58:
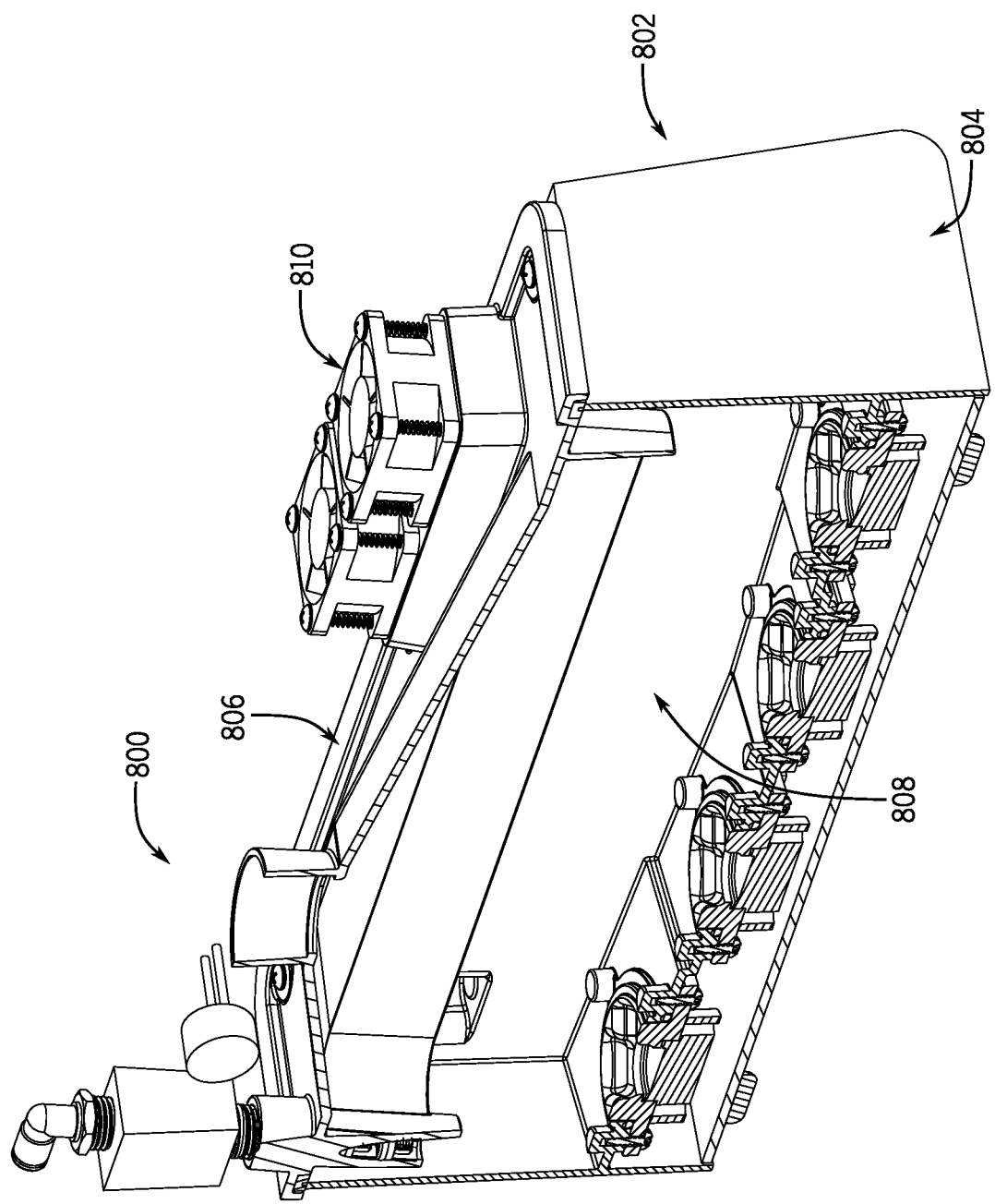
FIG. 58 is a front perspective cross-sectional view of the fog generator assembly of FIG. 56.
Figure 59:
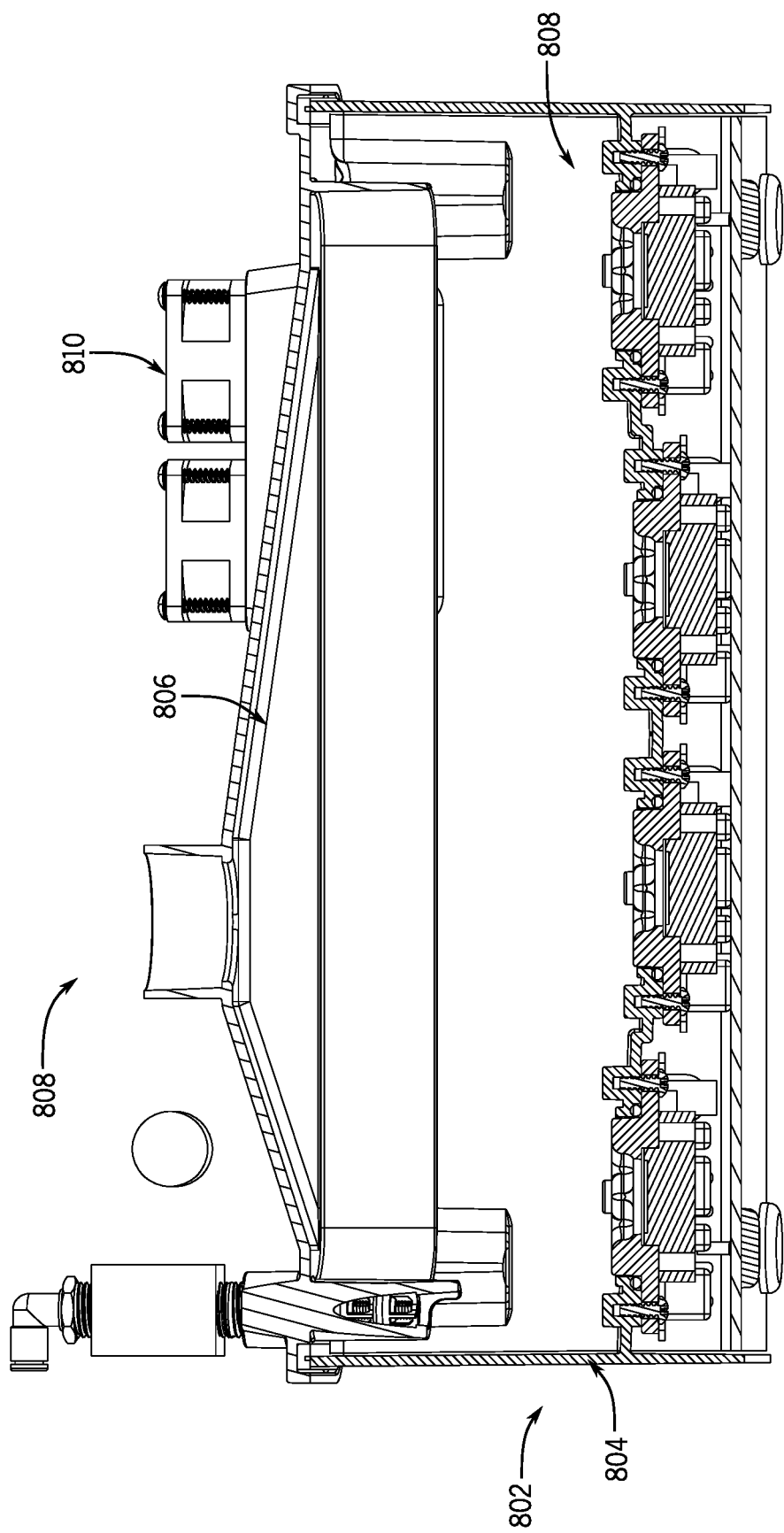
FIG. 59 is a back cross-sectional view of the fog generator assembly of FIG. 56, according to an exemplary embodiment.

A method 750 of operation for the aromatic sequence control system 700 is shown schematically in FIG. 55, according to an exemplary embodiment. The method 750 includes receiving a control signal from a control device, at 752. The control device may be one of a variety of different electronic devices (e.g., an IoT device, a mobile phone, a laptop computer, a handheld remote, etc.). A user may manually select a set of operating parameters or create an operating sequence including multiple different sets of operating parameters arranged temporally. A user may select the desired sequence of fragrances from a software application downloaded to the control device. For example, the user may be prompted to perform initial setup operations to assign fragrances to each chamber 116 in the support shelf 120. Alternatively, the control system 700 may include one or more sensors configured to detect the presence of a well 109 and/or a quantity of fluid in a well 109.

The user may utilize the software application to create a customized sequence of fragrances or a duration for each portion of the sequence. The user may additionally include periods where no fragrance is dispensed into the fog of water vapor, which can, advantageously, prevent a user from becoming desensitized to any of the individual fragrances being emitted into the user occupied space. In other embodiments, the user may include periods where fragrance is introduced without the presence of fog. In yet other embodiments, the release of fragrance may be coordinated with the activation or deactivation of the fog. For example, the release of different aromas may be linked with the activation or deactivation of fog such that the occupant of the bath is alerted to the change in fragrance. In some embodiments, the release of different aromas in the sequence may be linked with other operating parameters such as the changing of lighting (e.g., color, intensity, etc.). For example, the color of the light may change whenever a new fragrance is released.

In an exemplary embodiment, the software application may also be used to select a predetermined sequence. The predetermined sequence may be available to other users of the software application (e.g., the predetermined sequence may be saved to the Cloud, etc.). The sequence may include the ability to control the intensity and/or color of light emitted by the light source 112 and/or how the light and fog interact with the fragrance in each part of the sequence. The software application may also provide the user with the ability to tune or otherwise modify a characteristic of the fog of water vapor (e.g., particle size, intensity, etc.). For example, the software application may be configured to allow the user to select an intensity of fog, which may result in the activation of additional ultrasonic devices 210, alteration of an operating frequency of the ultrasonic devices 210, and/or alteration of a fan speed. Various alternative control schemes are possible through control of the light source 112, the fan 600, the plurality of ultrasonic devices 210, and the valve member 724.

The method 750 of FIG. 55 further includes activating the ultrasonic devices 210 and the fan 600, at 754. Operation 754 may include activating a number of ultrasonic devices 210 and/or an operating frequency for the fan 600 and ultrasonic devices 210 based on a first part of a predetermined operating sequence. The method 750 further includes repositioning the valve member 724, at 756, to provide a first fragrance. The method 750 additionally includes querying the control signal for changes to one or more operating parameters, at 758. The method 750 also includes monitoring the control signal for a shut-down command, at 760 (e.g., a command received at the end of a predetermined operating sequence that signals various system components to turn-off). If a shut-down command is received (at 762), the ultrasonic devices and the fan are deactivated. If a shut-down command has not been received, the system 700 is configured to evaluate whether the control signal indicates that the fragrance or aromatic should be changed, at 764 (e.g., whether to adjust the operating parameters of the various system components to match a second set of pre-specified parameters in an operating sequence, etc.). If the control signal indicates that the fragrance should be changed, the method 750 returns to operation 756 and repeats. In other embodiments, the method 750 may include additional, fewer, and/or different operations.

The configuration of the aromatic sequence control system 700 and associated control methods described in the exemplary embodiment of FIGS. 43 and 55 should not be considered limiting. Various alterations and substitutions may be made without departing from the inventive concepts described herein. For example, in some embodiments the valve member 724 may be replaced by a series of individual flow control valves (e.g., solenoid valves, etc.) configured to regulate the flow from each of the chambers 116. In such an embodiment, the number of active chambers 116 is not limited by the geometry of the slot 730 in the valve member 724.

Referring to FIGS. 56-64, a fog generator assembly 800 is shown, according to another exemplary embodiment. The fog generator assembly 800 is similar to the fog generator subassembly 200 described above, with a few differences. The details regarding the fog tank 206, ultrasonic devices 210, fans 600, water supply and metering system 216 provided above are applicable to the corresponding elements of the fog generator assembly 800. Accordingly, these details have been omitted from the following description of the various elements of the fog generator assembly 800 for the sake of efficiency.

In the exemplary embodiment shown in FIGS. 56-61, the fog generator assembly 800 is configured to provide a fog of water vapor to a user occupied space. Unlike the assembly 10 of FIGS. 2-3, the fog generator assembly 800 of FIGS. 56-61 is configured as a portable fog generator and can, advantageously, be repositioned anywhere within the bath environment (i.e., can be repositioned without having to decouple the fog generator assembly 800 from a supporting surface). The fog generator assembly 800 includes a housing 802 including a base 804 and a cover 806 disposed on the base 804. The cover 806 may be removably coupled to the base 804 using clips, or another suitable mechanical fastener to provide access for users/technicians during maintenance events. The base 804 includes a cavity 808 configured to contain a volume of water. The fog generator assembly 800 includes a plurality of ultrasonic devices 210 configured to generate an aerosolized mist/fog of water vapor, which is forced from the cavity 808 by a plurality of fans 810 configured to draw air from the surroundings into the cavity 808. In other exemplary embodiments, the fog generator assembly 800 is coupled to an aromatic dispensing system (e.g., via a duct fluidly coupled to an inlet to the fans 810, etc.). In yet other embodiments, the plurality of ultrasonic devices 210 may be replaced with one or more separate, self-contained ultrasonic fogger devices (e.g., the fogger device 252 of FIG. 41, etc.).

Figure 60:
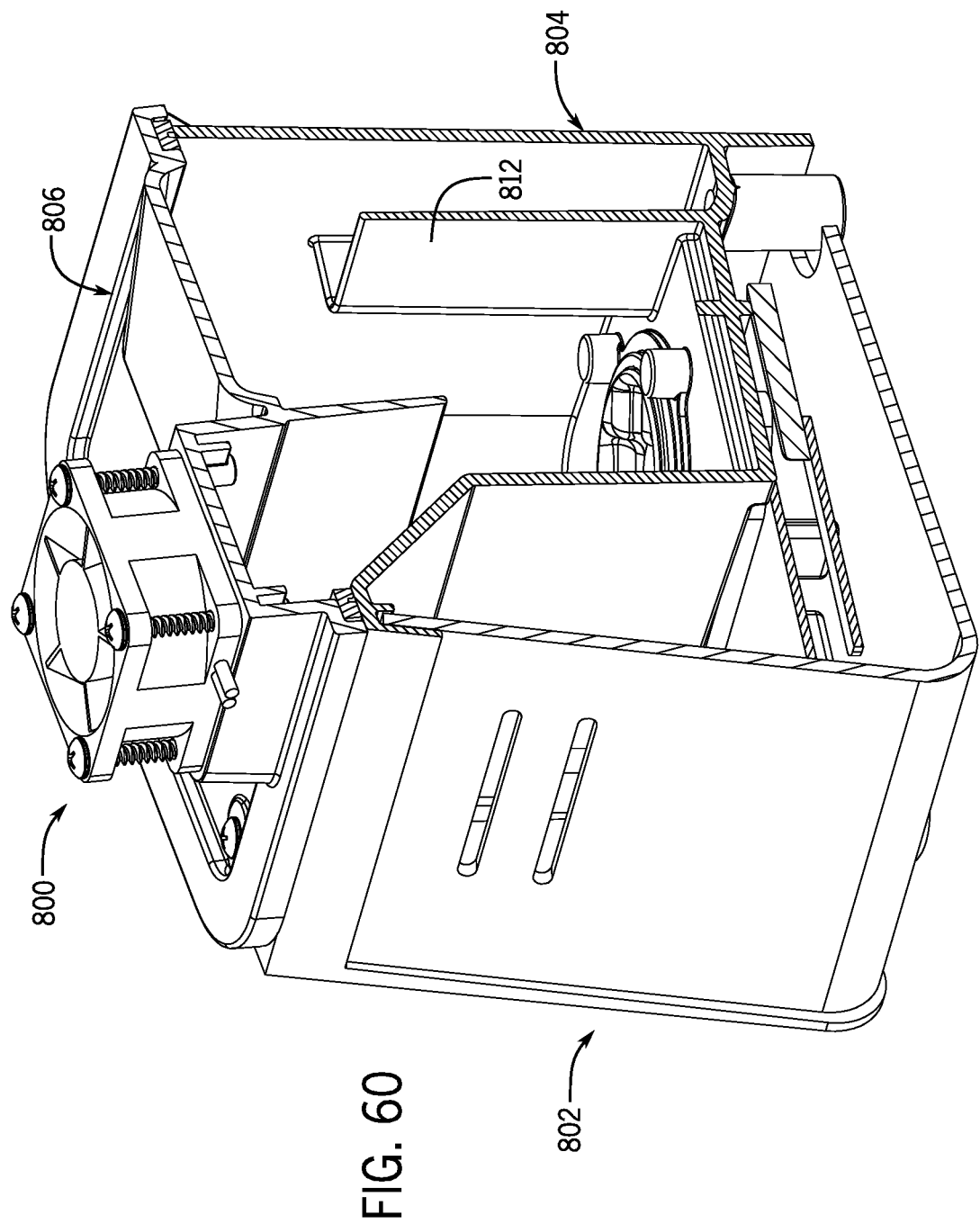
FIG. 60 is a back perspective cross-sectional view of the fog generator assembly of FIG. 56, according to an exemplary embodiment.
Figure 61:
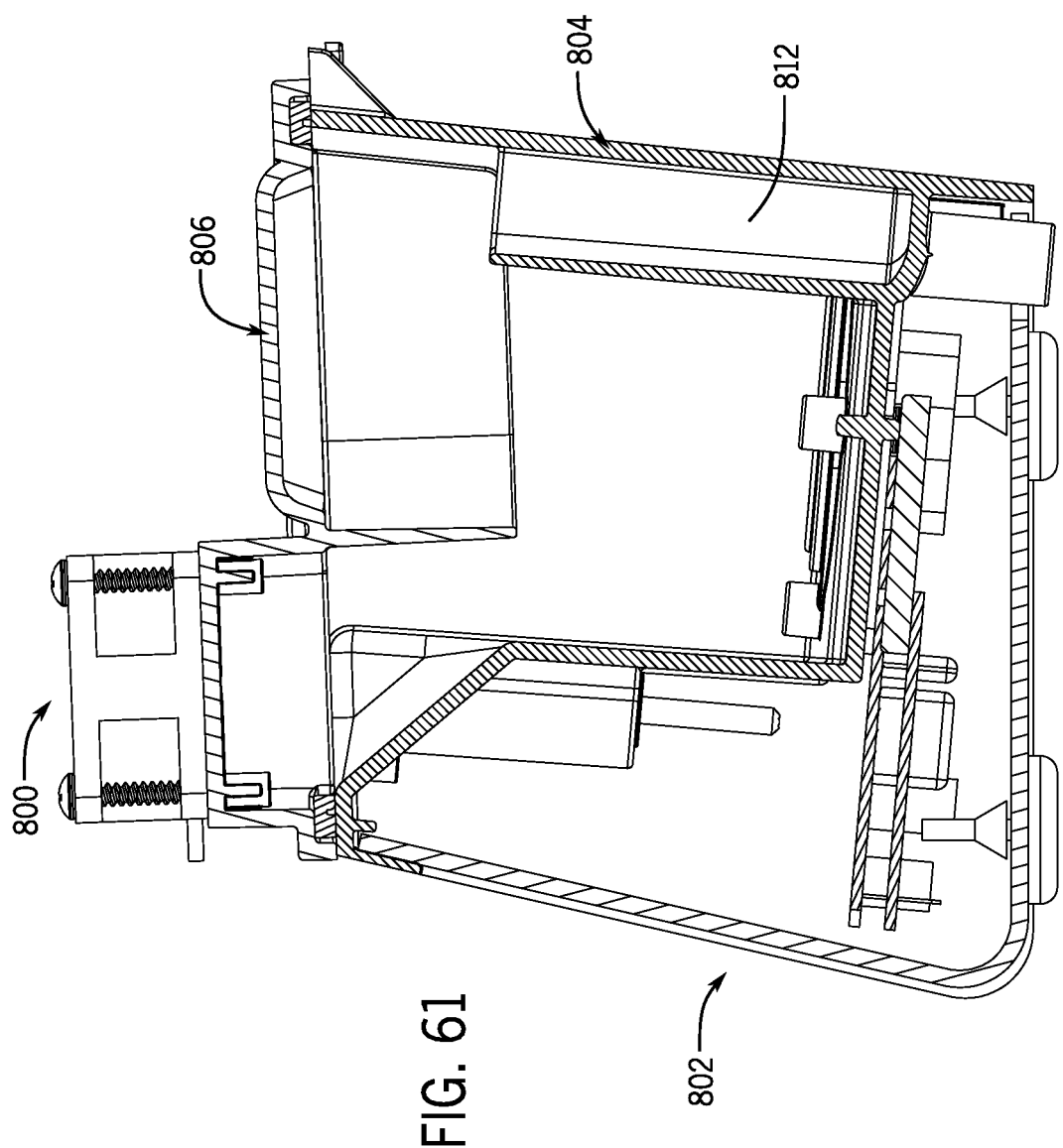
FIG. 61 is a side cross-sectional view of the fog generator assembly of FIG. 56, according to an exemplary embodiment.
Figure 62:
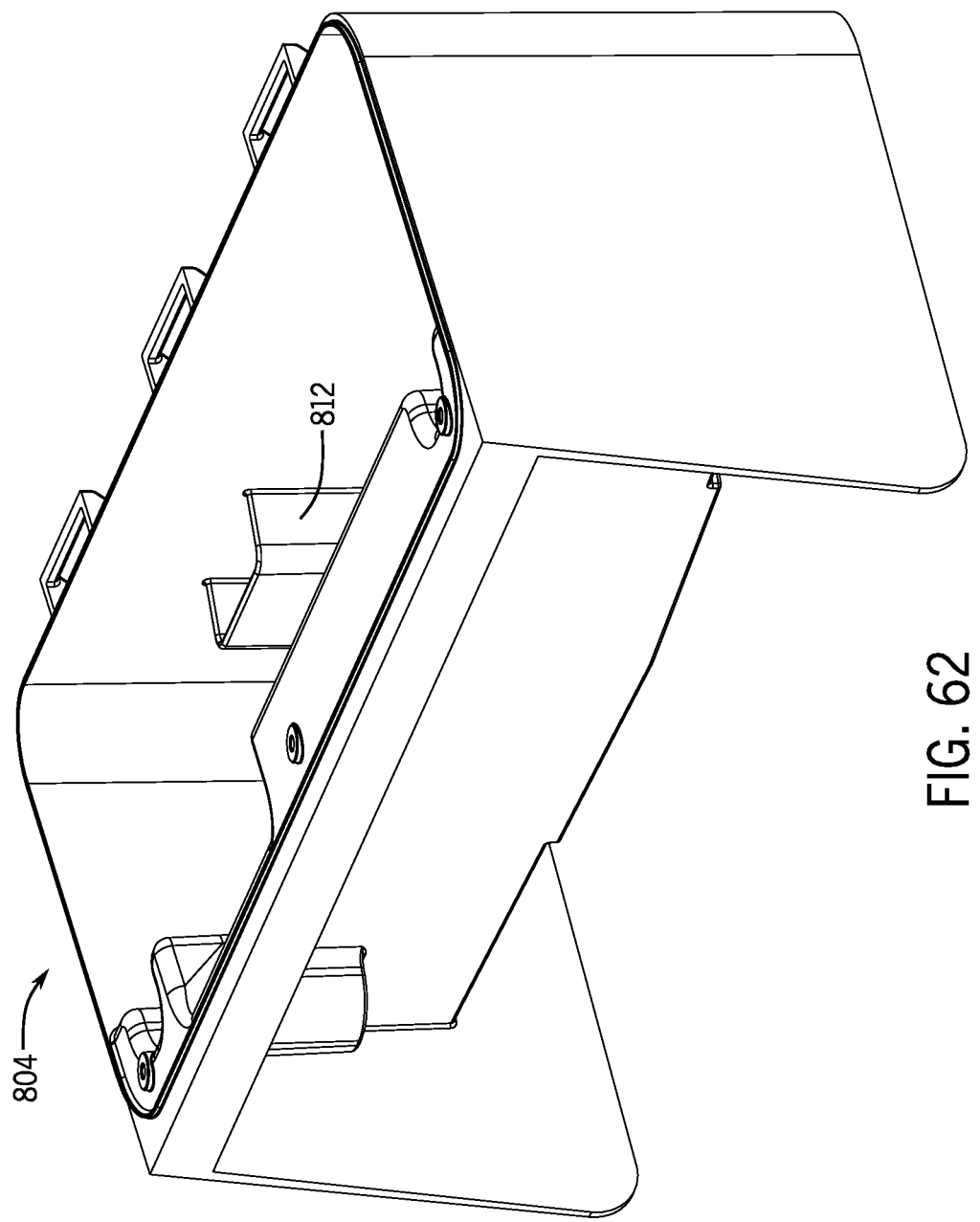
FIG. 62 is a back perspective view of a base for the fog generator assembly of FIG. 56, according to an exemplary embodiment.
Figure 63:
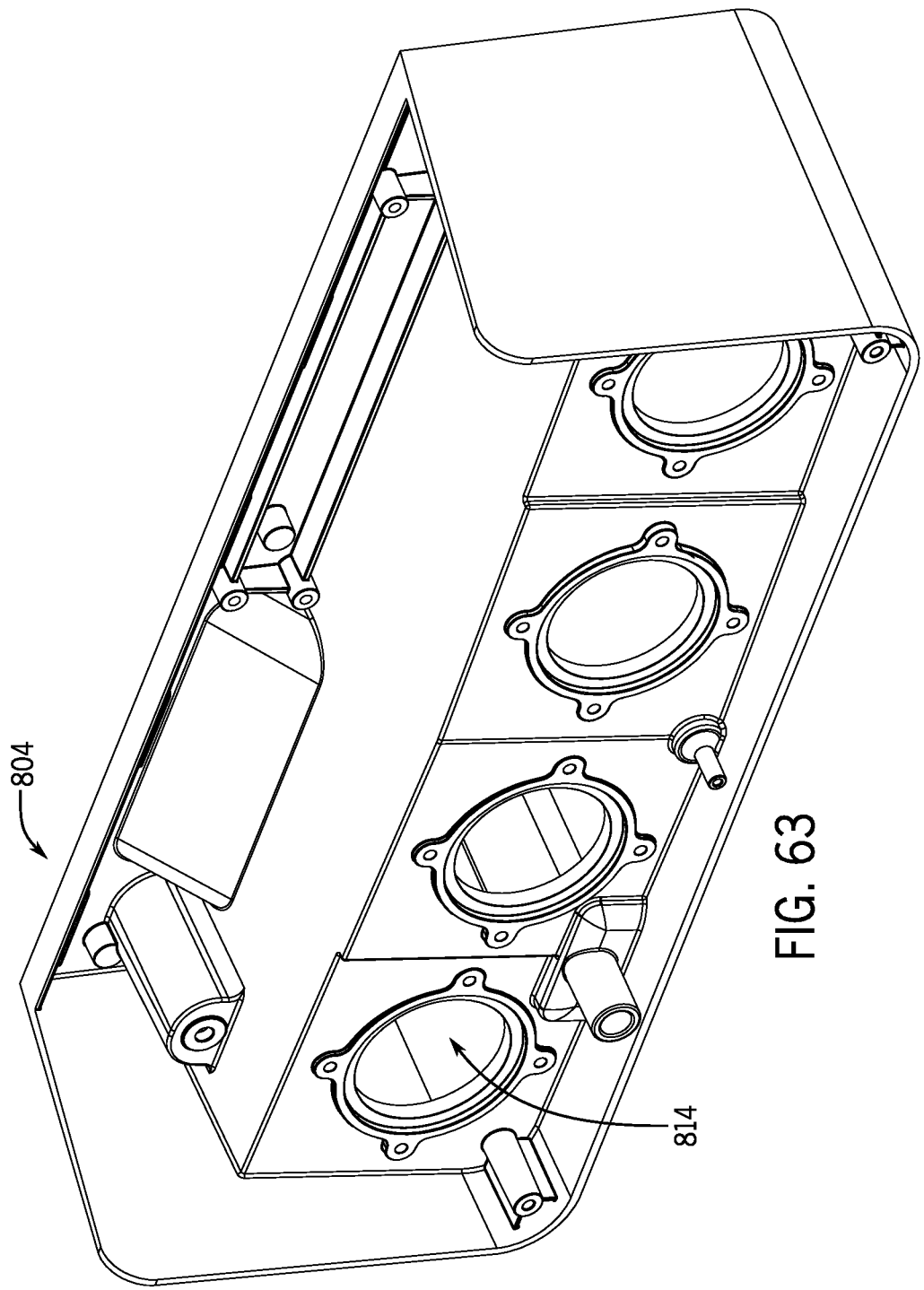
FIG. 63 is a bottom perspective view of the base of FIG. 56.

As shown in FIGS. 60-62, the base 804 includes an integrated overflow configured to prevent the water level from exceeding a predetermined threshold (e.g., a threshold based on a height of an overflow partition 812 in the base 804, etc.). The fog generator assembly 800 may alternatively, or additionally, include a flow control valve and/or level measurement sensor to facilitate metering of the water level in the base 804. As shown in FIG. 63, the base 804 includes a plurality of openings 814, each configured to receive a corresponding one of the ultrasonic devices 210.

Figure 64:
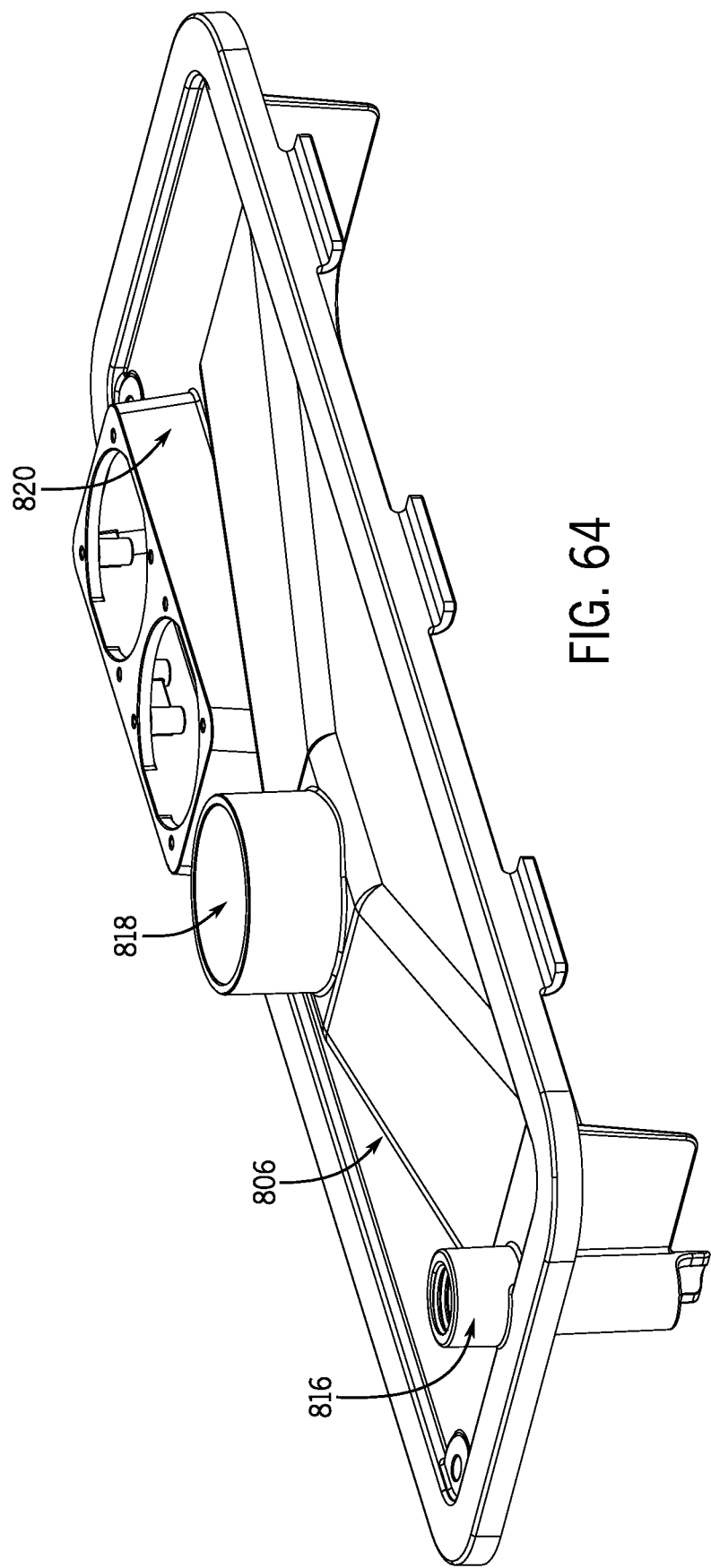
FIG. 64 is a perspective view of a cover for the fog generator assembly of FIG. 53, according to an exemplary embodiment.

An exemplary embodiment of the cover 806 for the fog generator assembly 800 is shown in FIG. 64. The cover 806 includes an inlet port 816 configured to receive a supply line from a water source, an outlet opening 818, and a fan platform 820 configured to receive and support the fans 810. In other exemplary embodiments, the cover 806 further includes a sensor support member configured to receive and support a liquid level measurement sensor.

The fog generator assembly, of which various exemplary embodiments are disclosed herein, provides several advantages over conventional devices. Among other benefits, the fog generator assembly produces a controllable fog of water vapor to cool a user or otherwise enhance the user's bathing experience. The fog generator assembly is self-contained and supported. The fog generator assembly also includes an aromatic dispensing portion, which is remotely controlled and configured to provide to the user a sequence of fragrances mixed with the fog of water vapor. The sequence of fragrances is controlled automatically and can be customized based on user preferences. The fog generator assembly includes a housing (e.g., a fog tank 206, a base 804, etc.) having a structural design that can help to prevent water from being retained within the fog generator assembly during periods of non-use, which can, advantageously, prevent the growth of mold or bacteria.

In various exemplary embodiments, the fog generator assembly is part of a whirlpool bathing system 21 that includes a whirlpool bath 20, as shown in FIG. 1. The whirlpool bathing system 21 further includes a whirlpool filtration system configured to remove visible particulate and/or impurities from the bath 20. In particular, the filtration system is configured to remove particulate from a water recirculation system (not shown) for the bath 20 that is used to pump water to different areas within the bath (e.g., water jets, etc.). The whirlpool filtration system is removably coupled to the recirculation system. The visible particulate may include large debris such as hair, dirt, and other debris which would otherwise cause the user to feel as if he/she is bathing in dirty water.

Figure 65:
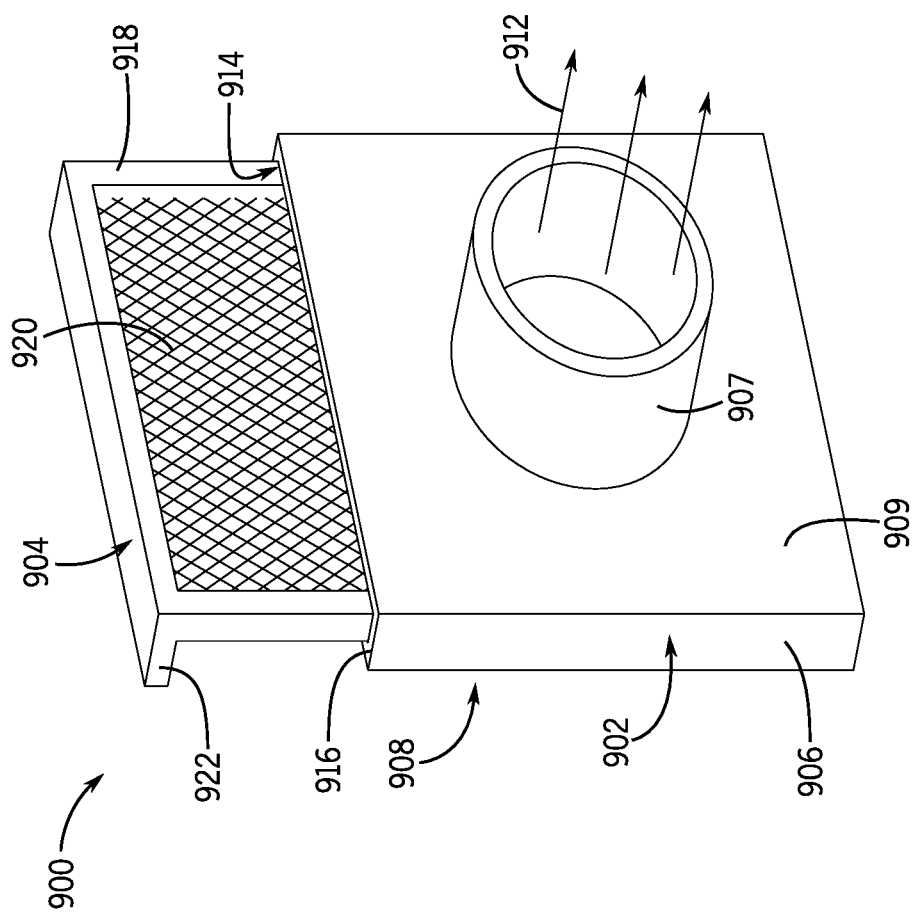
FIG. 65 is a perspective view of a whirlpool filtration system, according to an exemplary embodiment.

Referring now to FIG. 65, a whirlpool filtration system is shown as filtration system 900, according to an exemplary embodiment. In some embodiments, the filtration system 900 is disposed on a suction side of the recirculation system upstream of a pump of the recirculation system. In other embodiments, the location of the filtration system 900 may be different (e.g., the pressure side of the recirculation system downstream of the pump, at least partially within the bath 20, etc.). In the exemplary embodiment of FIG. 1, the filtration system 900 is disposed within the pedestal 23 and is concealed from a user's view by the pedestal 23. Water entering the pedestal 23 is routed (e.g., via shrouding, funnel structure, etc.) toward an inlet to the filtration system 900.

As shown in FIG. 65, the filtration system 900 includes a filter housing 902 and a filter element 904 (e.g., cartridge, etc.) removably coupled to the filter housing 902. The filter housing 902 includes a body 906 defining an inlet opening (not shown) on a first side 908 of the filter housing 902. The opening is sized to minimize the pressure drop across the filtration system 900. For example, the opening may have a cross-sectional area that is approximately the same as the total flow area through the filter element 904. The housing 902 also includes an outlet extension 907 extending outwardly from a forward surface 909 of the body 906 in substantially perpendicular orientation relative to the forward surface 909. As shown in FIG. 65, the outlet extension 907 is a flow tube (e.g., fluid conduit, etc.) configured to deliver fluid from the filter element 904 to the recirculation system (e.g., the pump, etc.).

As shown in FIG. 65, the body 906 has a rectangular cross-section normal to a flow direction 912 through the body 906. The body 906 defines a hollow cavity 914 configured to receive the filter element 904 therein. The body 906 supports the filter element 904 and prevents movement of the filter element 904 relative to the body 906 during normal operation. The filter element 904 is slidably coupled to the body 906. In the exemplary embodiment of FIG. 65, the filter element 904 is received within a rectangular slot (e.g., opening, etc.) disposed in an upper wall 916 of the body 906. When the filter element 904 is fully inserted into the body 906, the filter element 904 occludes the opening in the first side of the body 906 such that flow passing through the filter system 900 must pass through the filter element 904 before leaving through the outlet extension 907.

The filter element 904 includes a frame 918 and a filter media 920 disposed substantially within the frame 918. Specifically, the filter media 920 is disposed within a rectangular opening defined by the frame 918 such that the filter media 920 is surrounded by the frame 918. The frame 918 is configured to support the filter media 920 along a perimeter of the filter media 920 and to prevent deformation of the filter media 920 under an applied fluid pressure. The filter media 920 may be made from a synthetic mesh and may include nylon, polyester, and/or polypropylene. The frame 918 may be made from polyvinylchloride, nylon, and/or another suitable material.

As shown in FIG. 65, the frame 918 includes a tab 922 (e.g., a finger, a catch, etc.) disposed along an upper edge of the frame 918 and extending in substantially perpendicular orientation relative to the frame 918. The tab 922 is configured to engage with the upper wall 916 of the body 906 when the filter element 904 is fully inserted into the body 906. Among other benefits, the tab 922 facilitates removal of the filter element 904 from the body 906 when the filter media 920 becomes contaminated. In this way, the filter element 904 may be periodically removed from the body 906 to be cleaned (e.g., by rinsing with water, etc.).

The design of the filtration system 900 shown in FIG. 65 should not be considered limiting. Many alternatives are possible without departing from the inventive concepts disclosed herein. For example, FIGS. 66-68 show a retrofit filtration system 1000 that is configured to be received within an existing suction fitting 1002 of a whirlpool bath (e.g., in the base and/or lower portion of the whirlpool bath), according to an exemplary embodiment.

Figure 66:
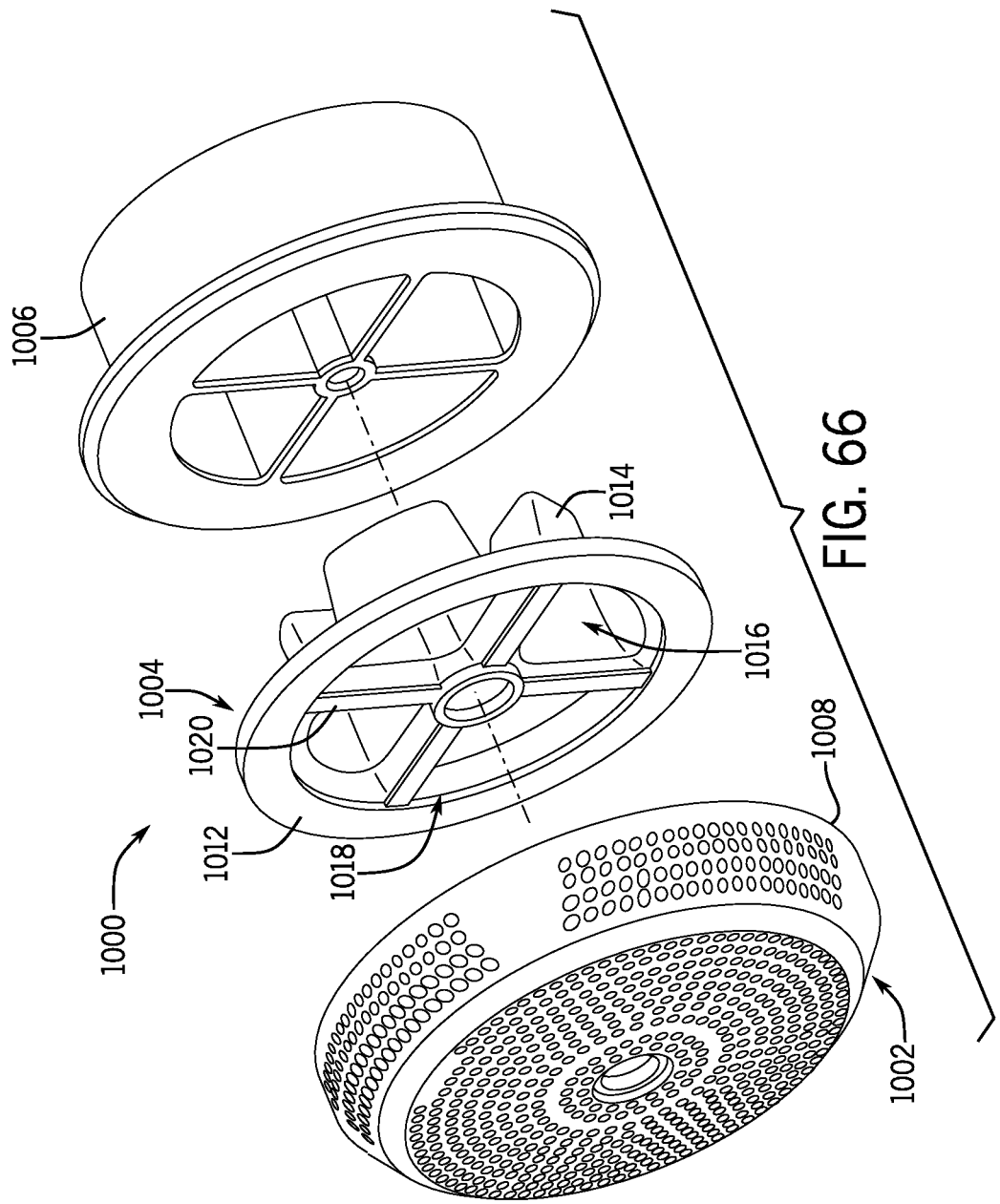
FIG. 66 is an exploded perspective view of a whirlpool filtration system, according to another exemplary embodiment.
Figure 67:
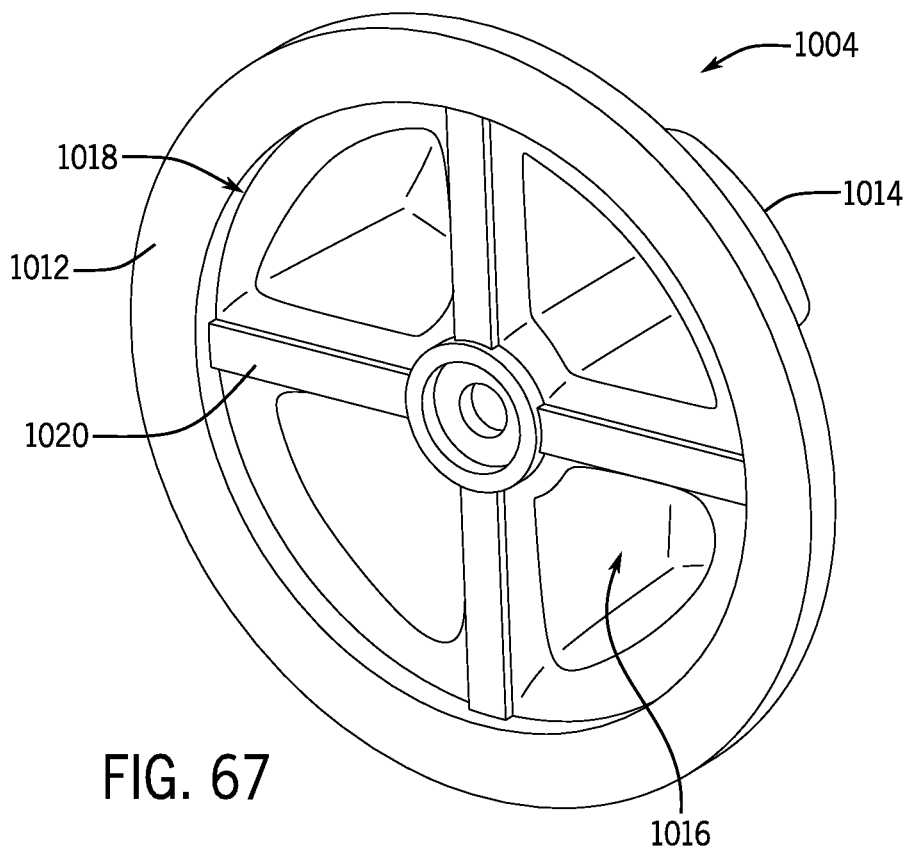
FIG. 67 is a rear front view of the whirlpool filtration system of FIG. 65.
Figure 68:
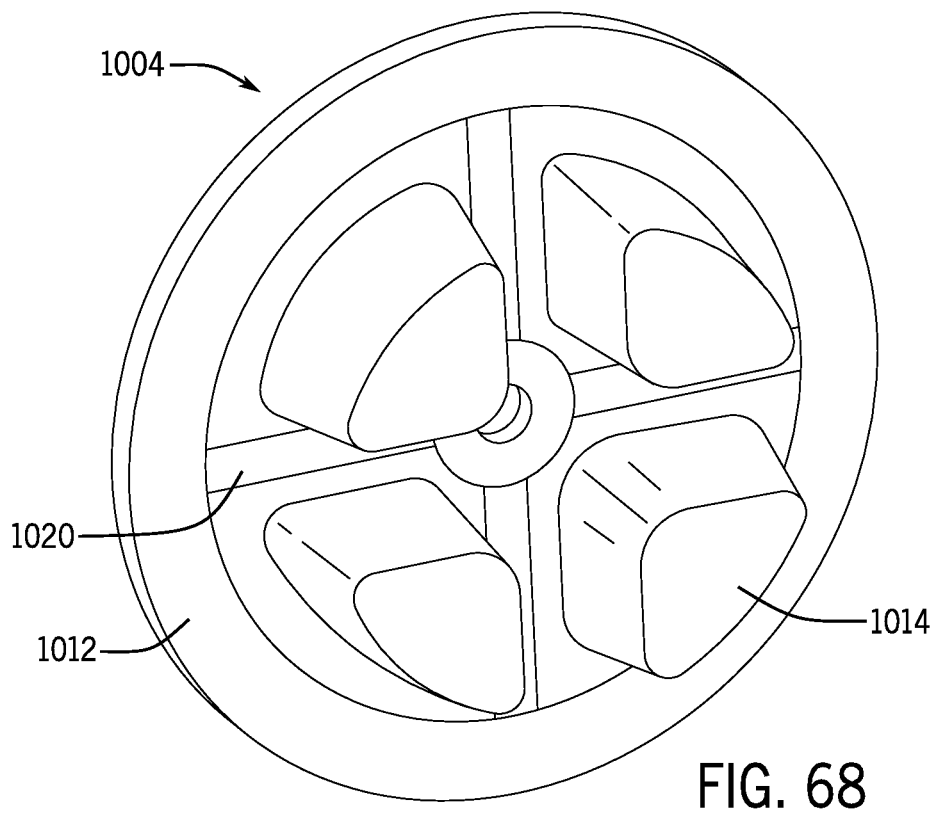
FIG. 68 is a rear perspective view of the whirlpool filtration system of FIG. 65.

As shown in FIGS. 66-68, the retrofit filtration system 1000 includes a filter element 1004 that is configured to fit within the suction fitting 1002 without modifying the suction fitting 1002, into a volume formed between the suction fitting 1002 and a wall of the bath. The suction fitting 1002 shown in FIGS. 66-68 includes an insert 1006 and a perforated top plate 1008 that is coupled to the insert 1006. The top plate 1008 engages the insert 1006 near an outer perimeter of the insert 1006 and is secured in place using a fastener (e.g., a bolt, screw, etc.) that passes through a central opening in both the top plate 1008 and the insert 1006.

As shown in FIGS. 66-68, the filter element 1004 is received within a volume (e.g., space, cavity, etc.) between the insert 1006 and the top plate 1008. The filter element 1004 includes a frame 1012 and a filter media 1014 coupled to the frame 1012. The materials for the frame 1012 and the filter media 1014 may be the same as or substantially similar to the frame 918 and the filter media 920 described with reference to FIG. 65. As shown in FIGS. 66-68, the filter media 1014 defines a plurality of pockets 1016 (e.g., four pockets 1016) that extend into openings 1018 of the insert 1006. The frame 1012 is coupled to the filter media 1014 along a perimeter of each one of the openings 1018, which prevents the filter media 1014 from being sucked in through the openings 1018 of the insert 1006. The frame 1012 engages an outer surface of the insert 1006, along a top lip of the insert 1006 and along dividers 1020 between each opening 1018. In the exemplary embodiment of FIGS. 66-68, any water passing through the insert 1006 must first pass through the filter element 1004. To service the filter element 1004, the top plate 1008 of the suction fitting 1002 is removed and the filter element 1004 separated from the insert 1006. The suction fitting 1002 may be removed by loosening and/or removing the fastener. In other embodiments, the suction fitting 1002 may be removably coupled to the bath using mechanical clips, a snap on cover, or another suitable fastening element. The filter element 1004 can then be cleaned and reinstalled into the suction fitting 1002.

Among other benefits, the filtration systems 900, 1000 of FIGS. 65-68 improve a user's bathing experience by preventing any debris or particulate from continuously recirculating through the bath during normal operation. The filtration systems 900, 1000 may be retrofit into an existing suction fitting of the bath and may be hidden within the suction fitting to improve the overall aesthetic of the bath.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the application as recited in the appended claims.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like, as used herein, mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

It is important to note that the construction and arrangement of the apparatus and control system as shown in the various exemplary embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments.

Other substitutions, modifications, changes and omissions may also be made in the design, operating conditions and arrangement of the various exemplary embodiments without departing from the scope of the present application. For example, any element disclosed in one embodiment may be incorporated or utilized with any other embodiment disclosed herein.

What is claimed is:

1. A fog generator assembly, comprising:
   a water vapor generator comprising a fog tank and an ultrasonic device coupled to the fog tank;
   a fragrance dispenser comprising an inlet opening and a fluid containing chamber downstream from the inlet opening;
   an air displacement device fluidly coupling the fluid containing chamber to the fog tank; and
   a mixing element downstream from the fog tank, the mixing element configured to mix a fog of water vapor from the water vapor generator with a fragrance from the fragrance dispenser to produce an aromatic fog.

2. The fog generator assembly of claim 1, wherein the mixing element is configured to deliver the aromatic fog to a space above a bath.

3. The fog generator assembly of claim 1, wherein the air displacement device is a fan that is structured to move air through the inlet opening and across the fluid containing chamber.

4. The fog generator assembly of claim 1, wherein an amount of the aromatic fog provided by the mixing element is controlled by the air displacement device.

5. The fog generator assembly of claim 1, wherein the fragrance dispenser is configured to dispense a plurality of different fragrances, wherein the fog generator assembly further comprises a flow control manifold that is fluidly coupled to the fragrance dispenser and the mixing element, and wherein the flow control manifold is configured to selectively control the transfer of each one of the plurality of fragrances from the fragrance dispenser to the mixing element.

6. The fog generator assembly of claim 5, wherein the flow control manifold is configured to mix at least two of the plurality of fragrances from the fragrance dispenser to form an aromatic mixture, and wherein the flow control manifold is configured to transfer the aromatic mixture from the fragrance dispenser to the mixing element.

7. The fog generator assembly of claim 5, wherein the flow control manifold forms part of an aromatic sequence control system that is configured to selectively control the release of at least two fragrances of the plurality of fragrances in a predefined sequence, and wherein the sequence may be varied using a control device.

8. The fog generator assembly of claim 1, further comprising a light source, wherein the fog generator assembly coordinates the release of the aromatic fog with light emitted from the light source.

9. The fog generator assembly of claim 1, further comprising a water delivery and metering system configured to provide water to the water vapor generator and continuously drain water from the water vapor generator.

10. The fog generator assembly of claim 1, wherein the fluid containing chamber is one of a plurality of wells that are removable from the fragrance dispenser.

11. The fog generator assembly of claim 1, further comprising a fog tank at an intersection between the water vapor generator, the fragrance dispenser, and the mixing element, the fog tank comprising an outer wall defining a cavity, and wherein the fog tank does not include any horizontal surfaces.

12. A bathing system, comprising:
    a bath; and
    a fog generator assembly disposed adjacent the bath, the fog generator assembly comprising:
      a water vapor generator comprising a fog tank and an ultrasonic device coupled to the fog tank;
      a fragrance dispenser comprising an inlet opening and a fluid containing chamber downstream from the inlet opening;
      an air displacement device fluidly coupling the fluid containing chamber to the fog tank; and
      a mixing portion downstream from the fog tank, the mixing portion configured to mix a fog of water vapor from the water vapor generator with a fragrance from the fragrance dispenser to produce an aromatic fog and deliver the aromatic fog toward the bath.

13. The bathing system of claim 12, wherein the air displacement device is a fan that is structured to move air through the inlet opening and across the fluid containing chamber.

14. The bathing system of claim 13, further comprising a water delivery and metering system configured to provide water to the water vapor generator and continuously drain water from the water vapor generator.

15. The bathing system of claim 12, wherein an amount of the aromatic fog provided by the mixing portion is controlled by the air displacement device.

16. The bathing system of claim 12, wherein the fragrance is a first fragrance of a plurality of fragrances, further comprising a flow control manifold that is fluidly coupled to the fragrance dispenser and the mixing portion, and wherein the flow control manifold is configured to selectively control the transfer of each one of the plurality of fragrances from the fragrance dispenser to the mixing portion.

17. The bathing system of claim 16, wherein the flow control manifold is configured to mix at least two of the plurality of fragrances from the fragrance dispenser to form an aromatic mixture, and wherein the flow control manifold is configured to transfer the aromatic mixture from the fragrance dispenser to the mixing portion.

18. The bathing system of claim 17, wherein the flow control manifold forms part of an aromatic sequence control system that is configured to selectively control the release of at least two fragrances of the plurality of fragrances in a predefined sequence, and wherein the sequence may be varied using a control device.

19. The bathing system of claim 12, further comprising a light source, wherein the fog generator assembly coordinates the release of the aromatic fog with light emitted from the light source.

20. The bathing system of claim 12, wherein the fluid containing chamber is one of a plurality of wells that are removable from the fragrance dispenser.

\* \* \* \* \*